United States Patent [19]
Barbier et al.

[11] Patent Number: 5,246,960
[45] Date of Patent: Sep. 21, 1993

[54] OXETANONES

[75] Inventors: Pierre Barbier, Rixheim, France; Fernand Schneider, Basel; Ulrich Widmer, Rheinfelden, both of Switzerland

[73] Assignee: Hoffmann-La Roche Inc., Nutley, N.J.

[21] Appl. No.: 944,853

[22] Filed: Sep. 14, 1992

Related U.S. Application Data

[60] Division of Ser. No. 495,809, Mar. 19, 1990, Pat. No. 5,175,186, which is a division of Ser. No. 134,322, Dec. 17, 1987, Pat. No. 4,931,463, which is a continuation of Ser. No. 809,353, Dec. 16, 1985, abandoned.

[30] Foreign Application Priority Data

Dec. 21, 1984 [CH] Switzerland ............... 6102/84
Sep. 12, 1985 [CH] Switzerland ............... 3934/85

[51] Int. Cl.⁵ ............... C07D 405/12; A61K 31/365
[52] U.S. Cl. ............... 514/422; 514/449; 514/824; 514/909
[58] Field of Search ............... 514/422, 449, 824, 909

[56] References Cited

U.S. PATENT DOCUMENTS

| | | | |
|---|---|---|---|
| 4,931,463 | 6/1990 | Barbier et al. | 514/422 |
| 5,175,186 | 12/1992 | Barbier et al. | 514/449 |

*Primary Examiner*—C. Warren Ivy
*Assistant Examiner*—A. Owens
*Attorney, Agent, or Firm*—George M. Gould; George W. Johnston; Ellen Ciambrone Coletti

[57] ABSTRACT

Racemic compounds of the formula

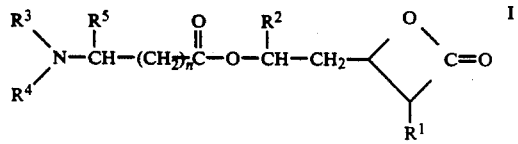

wherein $R^1$, $R^2$, $R^3$, $R^4$, $R^5$ and n are as described herein, enantiomers and diastereomers thereof, and salts of these esters with weak acids, are described. These compounds inhibit pancreas lipase and are useful agents in the treatment of obesity, hyperlipaemia, atherosclerosis and arteriosclerosis.

9 Claims, No Drawings

OXETANONES

This is a division of application Ser. No. 07/495,809 filed Mar. 19, 1990, now U.S. Pat. No. 5,175,186 which is a divisional of Ser. No. 134,322, filed Dec. 17, 1987, now U.S. Pat. No. 4,931,463 continuation of Ser. No. 06/809,353, filed Dec. 16, 1985, now abandoned.

BRIEF SUMMARY OF THE INVENTION

The invention relates to racemic oxetanones of the formula

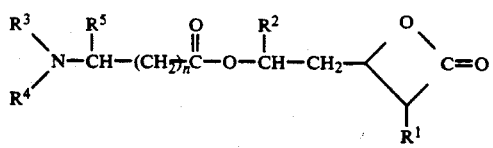

wherein $R^1$ and $R^2$ are independently $C_{1-17}$-alkyl which is saturated or optionally interrupted by up to 8 double or triple bonds and/or optionally interrupted by an O or S atom which is present in a position other than the α-position to an unsaturated C-atom; or phenyl, benzyl or $-C_6H_4-X-C_6H_5$ ring-substituted by up to 3 $C_{1-6}$-alkyl-(O or S) 1 or 0 groups, X is oxygen, sulfur or $(CH_2)_{0-3}$, $R^3$ is hydrogen, $C_{1-3}$-alkyl or $C_{1-3}$-alkanoyl, $R^4$ is hydrogen or $C_{1-3}$-alkyl, and $R^5$ is hydrogen, a group Ar or Ar-$C_{1-3}$-alkyl or $C_{1-7}$-alkyl optionally interrupted by Y and optionally substituted by Z, or $R^4$ forms with $R^5$ a 4-to 6-membered saturated ring, Y is oxygen, sulfur or a group $N(R^6)$, $C(O)N(R^6)$ or $N(R^6)C(O)$, Z is a group $-(O$ or $S)-R^7$, $-N(R^7,R^8)$, $-C(O)N(R^7, R^8)$ or $-N(R^7)C(O)R^8$, n is the number 1 or 0, with the proviso that $R^5$ is hydrogen when n is the number 1, Ar is phenyl which is unsubstituted or substituted by up to 3 groups $R^9$ or $OR^9$, and $R^6$, $R^7$, $R^8$ and $R^9$ individually are hydrogen or $C_{1-3}$-alkyl, with the proviso that $R^4$ is other than hydrogen when $R^3$ is formyl and $R^5$ is isobutyl or $R^3$ is acetyl and $R^5$ is carbamoylmethyl, and simultaneously $R^2$ is undecyl or 2,5-undecadienyl and $R^1$ is n-hexyl, enantiomers or diastereomers thereof, and salts of these oxetanones with weak acids.

The oxetanones of formula I are useful agents for inhibiting pancreas lipase, and accordingly are useful agents in treating obesity, hyperlipaemia, atherosclerosis and arteriosclerosis.

The invention also relates to a process for their preparation, intermediates which are usable in this process as well as medicaments based on the said oxetanones or based on precursors thereof.

DETAILED DESCRIPTION OF THE INVENTION

As used herein, the term "alkyl" denotes a straight or branched chain alkyl containing the number of carbon atoms designated. Examples of $C_1-C_{17}$-alkyl are methyl, ethyl, propyl, tertiary butyl, tridecyl allyl, and the like. The term "alkanoyl" denotes a straight or branch chained alkanoyl containing the number of carbon atoms designated. Examples of $C_1-C_3$ alkanoyl are formyl, acetyl and the like. The term 4- to 6-member saturated ring denotes a mono-$C_1$-$C_3$alkyl substituted or unsubstituted 4- to 6-member saturated, nitrogen containing ring, for example, pyrrolidinyl, 4-methylpyrrolidinyl, piperidinyl, and the like. The term "interrupted by an O or S atom or Y" as used in connection with the recitations of $R^1$, $R^2$, $R^4$ and $R^5$, denotes that the O or S atom or Y is a bridging atom or moiety positioned between two carbon atoms within the chain of $R^1$, $R^2$, $R^4$ or $R^5$ rather than an atom substituted off of the chain of $R^1$, $R^2$, $R^4$ or $R^5$. Examples of groups interrupted by an O or S atom or Y are methylthioethyl and methyloxyethyl. The term "$C_{1-6}$-alkyl-(O or S)$_{1\ or\ 0}$" denotes a $C_{1-6}$ alkyl optionally having an O or S, such as methyl, ethylthio, and ethyloxy.

The invention relates to racemic oxetanones of the formula

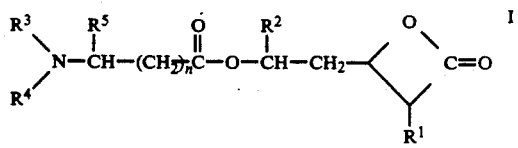

wherein $R^1$ and $R^2$ are independently $C_{1-17}$-alkyl which is saturated or optionally interrupted by up to 8 double or triple bonds and/or optionally interrupted by an O or S atom which is present in a position other than the α-position to a unsaturated C-atom; or phenyl, benzyl or $-C_6H_4-X-C_6H_5$ ring-substituted by up to 3 $C_{1-6}$-alkyl-(O or S)$_{1\ or\ 0}$ groups, X is oxygen, sulfur or $(CH_2)_{0-3}$, $R^3$ is hydrogen, $C_{1-3}$-alkyl or $C_{1-3}$-alkanoyl, $R^4$ is hydrogen or $C_{1-3}$-alkyl, and $R^5$ is hydrogen, a group Ar or Ar-$C_{1-3}$-alkyl or $C_{1-7}$-alkyl optionally interrupted by Y and optionally substituted by Z, or $R^4$ forms with $R^5$ a 4- to 6-membered saturated ring, Y is oxygen, sulfur or a group $N(R^6)$, $C(O)N(R^6)$ or $N(R^6)C(O)$, Z is a group $-(O$ or $S)-R^7$, $-N(R^7, R^8)$, $-C(O)N(R^7,R^8)$ or $-N(R^7)C(O)R^8$, n is the number 1 or 0, with the proviso that $R^5$ is hydrogen when n is the number 1, Ar is phenyl which is unsubstituted or substituted by up to 3 groups $R^9$ or $OR^9$, and $R^6$, $R^7$, $R^8$ and $R^9$ individually are hydrogen or $C_{1-3}$-alkyl, with the proviso that $R^4$ is other than hydrogen when $R^3$ is formyl and $R^5$ is isobutyl or $R^3$ is acetyl and $R^5$ is carbamoylmethyl, and simultaneously $R^2$ is undecyl or 2,5-undecadienyl and $R^1$ is n-hexyl, enantiomers or diastereomers thereof, and salts of these oxetanones with weak acids.

The invention also relates to a process for their preparation, intermediates which are usable in this process as well as medicaments based on the said oxetanones or based on precursors thereof.

Preferred oxetanones of the invention are compounds of formula I as described just above wherein $R^1$ is methyl, propyl, hexyl, decyl, hexadecyl, allyl, benzyl or ethyl; $R^2$ is methyl, undecyl, 3-butenyl, 3-undecenyl, 8,11-heptadecadienyl, phenoxy or heptadecyl; $R^3$ is acetyl or formyl; $R^4$ is methyl or hydrogen; and $R^5$ is hydrogen, methyl, 2-butyl, benzyl, methylthioethyl or i-butyl, or $R^4$ and $R^5$ together form a pyrrolidinyl residue.

Especially preferred oxetanones of the invention are compounds of formula I as described in the paragraph just above wherein $R^1$ is ethyl. Other especially preferred oxetanones of the invention are compounds of formula I as described in the paragraph just above wherein $R^2$ is heptadecyl. Other especially preferred oxetanones of the invention are compounds of formula I as described in the paragraph just above wherein $R^3$ is formyl. Other especially preferred oxetanones of the invention are compounds of formula I as described in the paragraph just above wherein $R^4$ is hydrogen. Other especially preferred oxetanones of the invention are compounds of formula I as described in the paragraph just above wherein R⁴ is hydrogen. Other especially preferred oxetanones of the invention are compounds of formula I as described in the paragraph just above wherein R⁵ is i-butyl.

Examples of compounds of formula I are:

N-Formyl-L-leucine 1-[(trans-3-ethyl-4-oxo-2-oxetanyl)methyl]dodecyl ester

N-formyl-L-leucine 1-[(trans-3-allyl-4-oxo-2-oxetanyl)methyl]dodecyl ester

N-formyl-(S)-leucine (S,9Z,12Z)-1-[(2S,3S)-3-ethyl-4-oxo-2-oxetanyl]methyl]-9,12-octadecadienyl ester N-formyl-(S)-leucine (S,Z)-1-[[(2S,3S)-3-ethyl-4-oxo-2-oxetanyl]methyl]-9-octadecenyl ester and N-formyl-(S)-leucine (R)-α-[[(2S,3S)-3-ethyl-4-oxo-2-oxetanyl]methyl]-p-phenoxybenzyl ester.

N-Formyl-(S)-leucine (S)-1-[[(2S,3S)-3-ethyl-4-oxo-2-oxetanyl]methyl]octadecyl ester is an especially preferred compound of formula I.

In another aspect the invention relates to racemic oxetanones of the formula

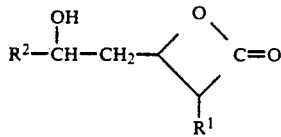   III wherein R¹ and R² are independently C₁₋₁₇alkyl which is saturated or optionally interrupted by up to 8 double or triple bonds and/or optionally interrupted by an O or S atom which is present in other than the α-position to an unsaturated C atom; or phenyl, benzyl or —C₆H₄—X—C₆H₅ ring-substituted by up to 3 C₁₋₆-alkyl-(O or S)₁ or 0 groups, and X is oxygen, sulfur or (CH₂)₀₋₃, with the proviso that when R¹ is n-hexyl and R² is undecyl or 2Z,5Z-undecadienyl, at least one of the asymmetric C-atoms present in the oxetanone ring and in the β-position to the latter has the R-configuration, enantiomers or diastereomers thereof.

Preferred oxetanones of the invention are compounds of formula III as described just above wherein R¹ is methyl, propyl, hexyl, decyl, hexadecyl, allyl, benzyl or ethyl; R² is methyl, undecyl, 3-butenyl, 3-undecenyl, 8,11-heptadecadienyl, phenoxy or heptadecyl.

Especially preferred oxetanones of the invention are compounds of formula III as described in the paragraph just above wherein R¹ is ethyl. Other especially preferred oxetanones of the invention are compounds of formula III as described in the paragraph just above wherein R² is heptadecyl.

Examples of compounds of formula III are:

((3S,4S)-4-Hexyl-4-[(R,10Z,13Z)-2-hydroxy-10,13-nonadecadienyl]-2-oxetanone;

rac-trans-3-Hexyl-4-[(10Z,13Z)-2-hydroxy-10,13-nonadecadienyl]]-2-oxetanone;

cis-3-Hexyl-4-[(10Z,13Z)-2-hydroxy-10,13-nonadecadienyl]-2-oxetanone;

3-Ethyl-4-[(Z)-2-hydroxy-10-nonadecenyl]-2-oxetanone;

rac-trans-3-Allyl-4-[2-hydroxytridecyl]-2-oxetanone; and trans-3-Hexyl-4-((R)-2-hydroxy-5-tridecenyl)-2-oxetanone.

rac-trans-3-Hexyl-4-(2-hydroxytridecyl)-2-oxetanone(2S,3S,4S:2R,3R,4R) is an especially preferred compound of formula III.

With weak acids, the oxetanones of formula I form salts which are likewise an object of the invention. Examples of such acids are p-toluenesulfonic acid, methanesulfonic acid, oxalic acid, ascorbic acid, fumaric acid, maleic acid, malic acid, citric acid and phosphoric acid.

The oxetanones of formula I can be prepared by
a) esterifying an acid of the formula

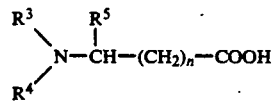   II which are known compounds or can be prepared according to known methods, or a functional derivative thereof with an alcohol of the formula

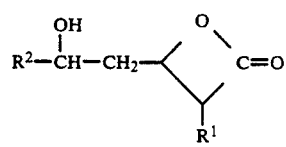   III wherein R¹-R⁵ and n are as described above, b) cleaving off the amino protecting group W in an oxetanone of the formula

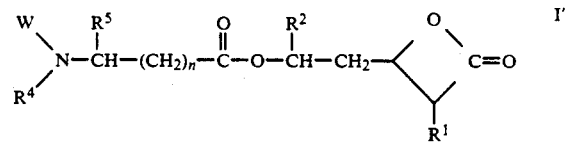   I' wherein R¹, R², R⁴, R⁵ and n are as described above, c) if desired, catalytically hydrogenating unsaturated moieties R¹ and R², d) if desired, C₁₋₃-alkanoylating oxetanones of formula I obtained in which at least one of R³ and R⁴ is hydrogen and an amino group Y or Z which may be present in R⁵ is tertiary, and e) if desired, isolating oxetanones of formula I obtained in the form of their salts with weak acids.

The oxetanones of formula I contain at least 3 asymmetric C atoms and the oxetanones of formula III can contain one or more asymmetric C atoms. They can accordingly be present as optically active enantiomers, as diastereomers or as mixtures, e.g. as racemic mixtures.

Unless otherwise indicated, the formulae in the specification are shown as racemates. The compounds of formula I contain at least 3 asymmetric C atoms and the compounds of formula III contain at least 1 assymmetric C atom. The compounds of formulae I and III can accordingly be present as and the invention encompasses optically active enantiomers, diastereomers, as well as racemates.

The esterification a) can be carried out in a solvent, e.g. an ether such as tetrahydrofuran (THF), in the presence of triphenylphosphine and diethyl azodicarboxylate, preferably at about room temperature. The corresponding anhydride can be used as the functional derivative of an acid of formula II.

Benzyloxycarbonyl and p-nitrobenzyloxycarbonyl can be mentioned as examples of an amino protecting group W in an oxetanone starting material I'. The cleavage reaction b) can be carried out by hydrogenation in a solvent, e.g. an ether such as THF, in the presence of a hydrogenation catalyst such as palladium-on-carbon (Pd/C), preferably at room temperature.

The optional hydrogenation (c) can be carried out under analogous conditions to the above-described cleavage reaction b).

The optional $C_{1-3}$-alkanoylation d) can be carried out in the presence of an acid anhydride, e.g. a mixed acid anhydride such as formic acid/acetic acid anhydride, in a solvent, e.g. an ether such as THF, preferably at room temperature.

The alcohols III can be prepared by cleaving off the ether protecting group L in an ether of the formula

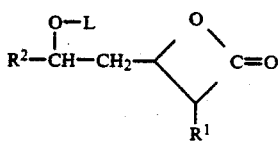

wherein $R^1$ and $R^2$ are as described above.

Tetrahydro-2H-pyran-2-yl, 1-ethoxyethyl, benzyl and t-butyldimethylsilyl are examples of ether protecting groups L.

The cleavage of the ether protecting group L can be carried out in a solvent, e.g. an alcohol such as ethanol, in the presence of pyridinium-4-toluenesulfonate while heating, e.g. to 50°–65° C.

The ethers IV can be prepared by cyclizing the acids of the formula

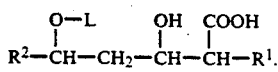

This reaction can be carried out in a solvent such as pyridine while cooling, e.g. to 0° C., in the presence of benzenesulfonyl chloride.

The acids V can be prepared either a) by saponifying a corresponding ester of the formula

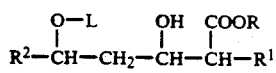

wherein R is $C_{1-4}$-alkyl and L, $R^1$ and $R^2$ are as described above, or b) by condensing an acid of the formula

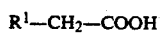

which are known compounds or can be prepared according to known methods, with an aldehyde of the formula

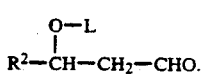

Methyl, ethyl and t-butyl are examples of alkyl moieties R. The saponification a) of an ester VI can be carried out with an alcoholic alkali metal or alkaline earth metal hydroxide solution such as a methanolic potassium hydroxide solution by heating at a temperature up to the reflux temperature of the reaction mixture.

The condensation b) of an acid VII with an aldehyde VIII can be carried out in a solvent such as THF in the presence of diisopropylamine and butyl lithium while cooling, e.g. to −50° C.

The acids V, which are present in the (5R)- or (5S)-form, can be converted in the following manner into the (2S,3S,5R)- or (2R,3R,5S)-stereoisomers:

A (5R)- or (5S)-acid of formula V is cyclized, e.g. by means of toluene-4-sulfonic acid monohydrate while heating to 50°–60° C. in ethanol, to the corresponding (6R)- or (6S)-pyranolone of the formula

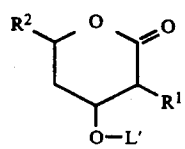

wherein L' is hydrogen and $R^1$ and $R^2$ are as described above.

This (6R)- or (6S)-pyranolone is then oxidized, e.g. in acetone by means of Jones' reagent at a temperature below 25° C., to the corresponding pyran-2,4-dione and the latter is stereospecifically hydrogenated, e.g. in ethyl acetate in the presence of platinum oxide, to the (3S,4S,6R)- or (3R,4R,6S)-pyranolone of formula V-A in which L' is hydrogen. This pyranolone is converted into a compound of formula V-A in which L' stands for an ether protecting group such as t-butyldimethylsilyl, e.g. by means of t-butyldimethylchlorosilane in dimethylformamide. The cyclic (3S,4S,6R)- or (3R,4R,6S)-ether obtained is cleaved, e.g. by reaction with an aqueous potassium hydroxide solution in dioxan, and the resulting compound is converted in situ into a (2S,3S,5R)- or (2R,3R,5S)-ether of the formula

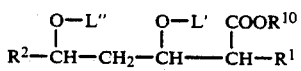

wherein L" is hydrogen, L' is the same ether protecting group as in the ether V-A, $R^{10}$ is benzyl or p-nitrobenzyl and $R^1$ and $R^2$ are as described above.

The ether V-B obtained is then converted into a diether of the same formula in which L" stands for an ether protecting group such as tetrahydro-2H-pyran-2-yl. After cleaving off firstly the ether protecting group L', e.g. with tetrabutylammonium fluoride trihydrate in THF, and then the group $R^{10}$, e.g. by hydrogenation in THF in the presence of Pd/C, there is obtained the desired (2S,3S,5R)- or (2R,3R,5S)-acid of formula V.

The esters VI can be prepared either a) by alkylating a corresponding ester of the formula

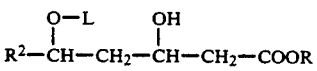

or b) by reducing a β-ketoester of the formula $$\begin{array}{ccc} \text{O}-\text{L} & \text{O} & \text{COOR} \\ | & \| & | \\ \text{R}^2-\text{CH}-\text{CH}_2-\text{C}-\text{CH}-\text{R}^1. \end{array} \quad \text{X}$$

The alkylation a) can be carried out by reacting an ester IX in a solvent such as THF with a solution of n-butyl lithium in a solvent such as n-hexane in the presence of diisopropylamine at about 50° C. and subsequently reacting with a solution of an alkyl halide ($R^1$-Hal), e.g. a bromide, in hexamethylphosphoric acid triamide at a temperature of about 0° to 10° C.

The reduction b) of a β-ketoester X can be carried out in an inert gas such as argon in a solvent such as THF with a complex metal hydride such as sodium borohydride ($NaBH_4$) at a temperature below 0° C.

The esters IX can be prepared by reductively removing the sulfoxide group in a sulfoxide of the formula $$\begin{array}{cccc} \text{OL} & \text{OH} & \text{COOR} & \diagup\text{O} \\ | & | & | & \\ \text{R}^2-\text{CH}-\text{CH}_2-\text{CH}-\text{CH}-\text{S} \\ & & & \diagdown\text{T} \end{array} \quad \text{XI}$$

wherein T is p-tolyl and L, R and $R^2$ are as described above.

This reaction can be carried out e.g. by means of aluminum amalgam in a solvent such as THF.

The β-ketoesters X can be prepared by reacting an aldehyde of the formula $R^2$—CHO, which are known compounds or can be prepared according to known methods, with a β-ketoester of the formula $$\begin{array}{c} \text{COOR} \\ | \\ \text{O}=\text{C}-\text{CH}-\text{R}^1 \\ | \\ \text{CH}_3 \end{array} \quad \text{XII}$$

which are known compounds or can be prepared according to known methods, and etherifying the resulting alcohol of the formula $$\begin{array}{ccc} \text{OH} & \text{O} & \text{COOR} \\ | & \| & | \\ \text{R}^2-\text{CH}-\text{CH}_2-\text{C}-\text{CH}-\text{R}^1. \end{array} \quad \text{XIII}$$

The preparation of an alcohol XIII and its etherification can be carried out as described e.g. in the following Examples H) and J)e), respectively.

Unsaturated moieties $R^1$ and $R^2$ which are present in the intermediates of formula I', III-VI, V-B, X and XIII can be hydrogenated if desired, e.g. under the conditions described above in connection with the hydrogenolytic cleavage of a group W or $R^{10}$.

The sulfoxides XI can be prepared by condensing an aldehyde of formula VIII above with an ester of the formula $$\begin{array}{c} \text{O} \\ \diagdown \\ \phantom{xx}\text{S}-\text{CH}_2-\text{COOR} \\ \diagup \\ \text{T} \end{array} \quad \text{XIV}$$

e.g. as described in Example G). Esters of formula XIV are known compounds or can be prepared in accordance with known methods.

The aldehydes VIII can be prepared by reducing an ester of the formula $$\begin{array}{c} \text{O}-\text{L} \\ | \\ \text{R}^2-\text{CH}-\text{CH}_2-\text{COOR} \end{array} \quad \text{XV}$$

e.g. with a di-($C_{1-4}$-alkyl)-aluminum hydride such as diisobutylaluminum hydride in a solvent such as toluene at a temperature of about −60° to −80° C.

The esters of formula XV can be prepared starting from the aldehydes of the formula $R^2$—CHO via the sulfoxides of the formula $$\begin{array}{ccc} & \text{OH} & \text{COOR} \quad \diagup\text{O} \\ & | & | \\ & \text{R}^2-\text{CH}-\text{CH}-\text{S} \\ & & \diagdown\text{T} \end{array} \quad \text{XVI}$$

and the esters of the formula $$\begin{array}{c} \text{OH} \\ | \\ \text{R}^2-\text{CH}-\text{CH}_2-\text{COOR} \end{array} \quad \text{XVII}$$

e.g. as described in paragraphs F)a), d) and f); G)b), d) and f) and J)b), d) and f) hereinafter.

Further, an ester of formula XV in which $R^2$ is 3-alkenyl can be prepared by the ozonolysis of an ester of the formula $$\begin{array}{cc} \text{CH}_2 & \text{O}-\text{L} \\ \| & | \\ \text{CH}-\text{CH}_2-\text{CH}-\text{CH}_2-\text{COOR} \end{array} \quad \text{XVIII}$$

which are known compounds or can be prepared according to known methods, and a Wittig reaction with the resulting aldehyde of the formula $$\begin{array}{cc} \text{O} & \text{O}-\text{L} \\ \| & | \\ \text{CH}-\text{CH}_2-\text{CH}-\text{CH}_2-\text{COOR} \end{array} \quad \text{XIX}$$

e.g. as described in Examples K) and L).

(R)-α-(Hydroxydiphenylmethyl)benzyl acetate can be used in place of a sulfinyl ester XIV for the conversion of an aldehyde of formula VIII or of an aldehyde of the formula $R^2$—CHO into the corresponding ester of formula IX or XVII, respectively. In this case there is obtained as an intermediate in place of a sulfoxide of formula XI or XVI the (R)-2-hydroxy-1,2,2-triphenylethyl ester corresponding to the alkyl esters of formula IX or XVII.

The oxetanones of formula I' can be prepared in the same manner as the oxetanones of formula I, e.g. as described in Example 2.15) hereinafter by esterifying an acid of formula II in which W is present in place of $R^3$ with an alcohol of formula III. In this esterification there can be used instead of the aforementioned acid the acid anhydride obtained by reaction with N-ethyl-N'-(3-dimethylaminopropyl)-carbodiimide hydrochloride or preferably with dicyclohexylcarbodiimide, which can be carried out as described in Example 10 B.1).

The preparation of intermediates of formula IV to XIX is described in more detail in the following paragraphs A) to M). The compounds reacted as described in paragraphs A) to M), are either known compounds, compounds which can be prepared by known methods, or intermediates of the invention such as those of formula IV to XIX.

A) Preparation of the ethers of formula IV

A)a) 0.57 g of a diastereomer mixture which consisted, inter alia, of (2S,3S,5R,13Z,16Z)-2-hexyl-3-hydroxy-5-[(tetrahydro-2H-pyran-2-yl)oxy]-13,16-docosadienoic acid was dissolved in 10 ml of pyridine and cooled to 0° C. After the dropwise addition of 0.28 ml of benzenesulfonyl chloride the mixture was stirred at 0° C. for a long time. The reaction mixture was poured into 120 ml of 10 percent aqueous sodium chloride solution and extracted three times with 30 ml of diethyl ether. The combined extracts were dried, filtered and evaporated. After chromatography over silica gel there was obtained a diastereomer mixture of 3-hexyl-4-[(10Z,13Z)-2-[(tetrahydro-2H-pyran-2-yl)oxy]-10,13-nonadecadienyl]-2-oxetanones as a colorless oil, IR: 1815 cm$^{-1}$.

In an analogous manner,

A)b) 3-Ethyl-4-[(10Z,13Z)-2-[(tetrahydro-2H-pyran-2-yl)oxy]-10,13-nonadecadienyl]-2-oxetanone, IR: 1820 cm$^{-1}$, was obtained
from (13Z,16Z)-2-ethyl-3-hydroxy-5-[(tetrahydro-2H-pyran-2-yl)oxy]-13,16-docosadienoic acid;

A)c) (3S,4S)-3-ethyl-4-[(R,Z)-2-[(tetrahydro-2H-pyran-2-yl)oxy]-10-nonadecenyl-2-oxetanone was obtained
from (2S,3S,5R,Z)-2-ethyl-3-hydroxy-5-[(tetrahydro-2H-pyran-2-yl)oxy]-13-docosenoic acid;

A)d) (3-benzyl-4-[(10Z,13Z)-2-[(tetrahydro-2H-pyran-2-yl)oxy]-10,13-nonadecadienyl]-2-oxetanone, IR: 1818 cm$^{-1}$, was obtained
from (13Z,16Z)-2-benzyl-3-hydroxy-5-[(tetrahydro-2H-pyran-2-yl)oxy]-13,16-docosadienoic acid;

A)e) (3S,4S)-3-ethyl-4-[(S)-p-phenoxy-β-[(tetrahydro-2H-pyran-2-yl)oxy]phenethyl]-2-oxetanone was obtained
from (2S,3S,5S)-2-ethyl-3-hydroxy-5-(p-phenoxyphenyl)-5-[(tetrahydro-2H-pyran-2-yl)oxy]valeric acid;

A)f) (3S,4S)-3-hexyl-4-[(S)-p-phenoxy-β-[(tetrahydro-2H-pyran-2-yl)oxy]phenethyl-2-oxetanone, IR: 1815 cm$^{-1}$, was obtained
from (2S,3S,5S)-2-hexyl-3-hydroxy-5-(p-phenoxyphenyl)-5-[(tetrahydro-2H-pyran-2-yl)oxy]valeric acid;

A)g) 3-hexyl-4-[2-[(tetrahydro-2H-pyran-2-yl)oxy]tridecyl]-2-oxetanone was obtained
from 2-hexyl-3-hydroxy-5[(tetrahydro-2H-pyran-2-yl)oxy]hexadecanoic acid;

A)h) 3-hexyl-4-[(R)-2-[(tetrahydro-2H-pyran-2-yl)oxy]tridecyl]-2-oxetanone was obtained
from 2-hexyl-3-hydroxy-(R)-5[(tetrahydro-2H-pyran-2-yl)oxy]hexadecanoic acid;

A)i) 3-ethyl-4-[2-[(tetrahydro-2H-pyran-2-yl)oxy]tridecyl]-2-oxetanone was obtained
from 2-ethyl-3-hydroxy-5-[(tetrahydro-2H-pyran-2-yl)oxy]hexadecanoic acid;

A)j) 3-methyl-4-[(R)-2-[(tetrahydro-2H-pyran-2-yl)oxy]tridecyl]-2-oxetanone was obtained
from 2-methyl-3-hydroxy(R)-5-[(tetrahydro-2H-pyran-2-yl)oxy]hexadecanoic acid;

A)k) 3-allyl-4-[2-[(tetrahydro-2H-pyran-2-yl)oxy]tridecyl]-2-oxetanone was obtained
from 2-allyl-3-hydroxy-5-[(tetrahydro-2H-pyran-2-yl)oxy]hexadecanoic acid;

A)l) 3-hexyl-4-[(R)-2-[(tetrahydro-2H-pyran-2-yl)oxy]propyl]-2-oxetanone was obtained
from 2-hexyl-3-hydroxy(R)-5-[(tetrahydro-2H-pyran-2-yl)oxy]hexanoic acid;

A)m) 3-hexadecyl-4-[2-[(tetrahydro-2H-pyran-2-yl)oxy]propyl]-2-oxetanone was obtained
from 2-hexadecyl-3-hydroxy(R)-5-[(tetrahydro-2H-pyran-2-yl)oxy]hexanoic acid;

A)n) 3-hexyl-4-[(2-[(tetrahydro-2H-pyran-2-yl)oxy]-5-hexenyl]-2-oxetanone was obtained
from 2-hexyl-3-hydroxy-5-[(tetrahydro-2H-pyran-2-yl)oxy]nonenoic acid;

A)o) 3-decyl-4-(R)-2-[(tetrahydro-2H-pyran-2-yl)oxy]-5-hexenyl]-2-oxetanone was obtained
from 2-decyl-3-hydroxy(R)-5-[(tetrahydro-2H-pyran-2-yl)oxy]nonenoic acid;

A)p) 3-hexyl-4-[(R)-2-[(tetrahydro-2H-pyran-2-yl)oxy]-5-tridecenyl]-2-oxetanone was obtained
from 2-hexyl-3-hydroxy(R)-5-[(tetrahydro-2H-pyran-2-yl)oxy]hexadecenoic acid;

A)q) 3-hexyl-4-[(R)-2-[tetrahydro-2H-pyran-2yl)oxy]-5-hexenyl]-2-oxetanone was obtained
from 2-hexyl-3-hydroxy-(R)-5-[(tetrahydro-2H-pyran-2-yl)oxy]nonenoic acid.

B) Preparation of the acids of formula V

B)a) 1.0 g of the diastereomer mixture t-butyl (13Z,16Z)-2-hexyl-3-hydroxy-5-[(tetrahydro-2H-pyran-2-yl)oxy]-13,16-docosadienoate was heated to reflux in 17 ml of a 2N methanolic potassium hydroxide solution until the starting material had disappeared. The reaction mixture was cooled and poured on to 60 ml of icewater. The mixture was adjusted to pH 1 by the dropwise addition of 1M aqueous hydrochloric acid and thereupon exhaustively extracted with ether. The combined ether phases were dried, filtered and evaporated. The oil was chromatographed on silica gel, whereby a diastereomer mixture of (13Z,16Z)-2-hexyl-3-hydroxy-5-[(tetrahydro-2H-pyran-2-yl)oxy]-13,16-docosadienoic acid was obtained an oil, IR: 3350, 1709, 1132, 1078, 1023 cm$^{-1}$.

In an analogous manner,

B)b) (13Z,16Z)-2-ethyl-3-hydroxy-5-[(tetrahydro-2H-pyran-2-yl)oxy]-13,16-docosadienoic acid was obtained
from t-butyl (13Z,16Z)-2-ethyl-3-hydroxy-5-[(tetrahydro-2H-pyran-2-yl)oxy]-13,16-docosadienoate;

B)c) (2S,3S,5R,Z)-2-ethyl-3-hydroxy-5-[(tetrahydro-2H-pyran-2-yl)oxy]-13-docosenoic acid was obtained
from t-butyl (2S,3S,5R,Z)-2-ethyl-3-hydroxy-5-[(tetrahydro-2H-pyran-8-yl)oxy]-13-docosenoate;

B)d) (13Z,16Z)-2-benzyl-3-hydroxy-5-[(tetrahydro-2H-pyran-2-yl)oxy]-13,16-docosadienoic acid, MS: 458 (M+-dihydropyran); IR: 3008, 1709, 1160, 1134, 1115 cm$^{-1}$, was obtained
from t-butyl (13Z,16Z)-2-benzyl-3-hydroxy-5-[(tetrahydro-2H-pyran-2-yl)oxy]-13,16-docosadienoate;

B)e) (2S,3S,5S)-2-ethyl-3-hydroxy-5-(p-phenoxyphenyl)-5-[(tetrahydro-2H-pyran-2-yl)oxy]valeric acid was obtained
from t-butyl (2S,3S,5S)-2-ethyl-3-hydroxy-5-(p-phenoxyphenyl)-5-[(tetrahydro-2H-pyran-2-yl)oxy]valerate;

B)f) (2S,3S,5R)-2-hexyl-3-hydroxy-5-(p-phenoxyphenyl)-5-[(tetrahydro-2H-pyran-2-yl)oxy]valerate was obtained
from t-butyl (2S,3S,5R)-2-hexyl-3-hydroxy-5-(p-phenoxyphenyl)-5-[(tetrahydro-2H-pyran-2-pyran-2-yl)oxy]valerate;

B)g) 2-hexyl-3-hydroxy-(R)-5-[(tetrahydro-2H-pyran-2-yl)-oxy]hexadecanoic acid was obtained from t-butyl-2-hexyl-3-hydroxy-(R)-5-[(tetrahydro-2H-pyran-2-yl)oxy]hexadecanoate;

B)h) 2-hexyl-3-hydroxy-5-[(tetrahydro-2H-pyran-2-yl)oxy]-hexadecanoic acid was obtained
from methyl 2-hexyl-3-hydroxy-5-[(tetrahydro-2H-pyran-2-yl)oxy]hexadecanoate.

C) Preparation of the acids V (variant)

C)a) 2 ml of diisopropylamine in 30 ml of dry THF were cooled to −20° C. and thereupon 9.68 ml of butyl lithium (1.6M/hexane) were added dropwise in such a manner that the temperature did not exceed −20° C. The mixture was subsequently stirred for 15 minutes and then cooled to −50° C. Thereafter, 0.720 ml of 4-pentenoic acid in 10 ml of THF was added dropwise and the mixture was stirred at 50° C. for a further 10 minutes. The mixture was stirred at room temperature for 1 hour and subsequently again cooled to −50° C. 2 g of rac-3-[(tetrahydro-2H-pyran-2-yl)oxy]-tetradecanal in 10 ml of THF were now added dropwise and the mixture was stirred at −50° C. for a further 30 minutes, then at room temperature for 72 hours. After hydrolysis with 2N hydrochloric acid the reaction mixture was evaporated. The residue was extracted with ether. The organic phase was dried over sodium sulfate, filtered and evaporated. The material obtained was filtered through a column of silica gel. There was obtained 2-allyl-3-hydroxy-5-[(tetrahydro-2H-pyran-2-yl)oxy]-hexadecanoic acid.

In an analogous manner.

C)b) 2-ethyl-3-hydroxy-5-[(tetrahydro-2H-pyran-2-yl)oxy]hexadecanoic acid was obtained
from rac-3-[(tetrahydro-2H-pyran-2-yl)oxy]tetradecanal and butanoic acid;

C)c) 2-methyl-3-hydroxy(R)-5-[(tetrahydro-2H-pyran-2-yl)oxy]hexadecanoic acid was obtained
from (R)-3-[(tetrahydro-2H-pyran-2-yl)oxy]tetradecanal and propionic acid;

C)d) 2-hexyl-3-hydroxy(R)-5-[(tetrahydro-2H-pyran-2-yl)oxy]hexanoic acid was obtained
from (R)-3-[(tetrahydro-2H-pyran-2yl)oxy]butanal and octanoic acid;

C)e) 2-hexadecyl-3-hydroxy-5-[(tetrahydro-2H-pyran-2-yl)oxy]hexanoic acid was obtained
from 3-[tetrahydro-2H-pyran-2-yl)oxy]butanal and octadecanoic acid;

C)f) 2-hexyl-3-hydroxy-(R)-5[(tetrahydro-2H-pyran-2-yl)oxy]-8-nonenoic acid was obtained
from (R)-3-[(tetrahydro-2H-pyran-2-yl)oxy]-6-heptenal and octanoic acid;

C)g) 2-decyl-3-hydroxy-(R)-5[(tetrahydro-2H-pyran-2-yl)oxy]-8-nonenoic acid was obtained
from (R)-3-[(tetrahydro-2H-pyran-2-yl)oxy]-6-heptenal and dodecanoic acid;

C)h) 2-hexyl-3-hydroxy-(R)-5[(tetrahydro-2H-pyran-2-yl)oxy]-8-pentadecenoic acid was obtained
from (R)-3-[(tetrahydro-2H-pyran-2-yl)oxy]-6-tetradecenal and octanoic acid;

C)i) 2-hexyl-3-hydroxy-5[(tetrahydro-2H-pyran-2-yl)oxy]-8-nonenoic acid was obtained
from 3-[(tetrahydro-2H-pyran-2-yl)oxy]-6-heptenal and octanoic acid.

D) Preparation of the esters of formula VI

D)a) 3.1 ml of diisopropylamine were cooled to −5° C. under argon and treated dropwise with 14 ml of about 1.6M n-butyl lithium solution in n-hexane. Thereafter, the mixture was stirred for 10 minutes. After cooling to −50° C. the cooling bath was removed and a solution of 5.08 g of a diastereomer mixture of butyl (13Z,16Z)-3-hydroxy-5-[(tetrahydro-2H-pyran-2-yl)oxy]-13,16-docosadienoate in 5 ml of THF was added dropwise. In so doing the temperature rose to −20° C. The mixture was left to warm to 0° C. and was stirred for 10 minutes. A solution of 2.1 ml of 1-bromohexane in 2.5 ml of hexamethylphosphoric acid triamide was then added, whereby the temperature rose to 9° C. Thereafter, the mixture was left to warm to room temperature and was stirred for 2½ hours. The solution was poured on to 200 ml of ice-water and saturated with sodium chloride. The mixture was extracted with ether. The combined extracts were dried, filtered and evaporated. The residual oil was chromatographed on silica gel. There was obtained a diastereomer mixture of t-butyl (13Z,16Z)-2-hexyl-3-hydroxy-5-[(tetrahydro-2H-pyran-2-yl)oxy]-13,16-docosadienoate, MS: 519 (M+-(CH$_3$)$_3$CO.); IR: 3503, 1728, 1709, 1153.

In an analogous manner,

D)b) t-butyl (13Z,16Z)-2-ethyl-3-hydroxy-5-[(tetrahydro-2H-pyran-2-yl)oxy]-13,16-docosadienoate, MS: 396 (M+-dihydropyran-isobutylene): IR: 3510, 1728, 1153, 1137 cm$^{-1}$, was obtained
from t-butyl (13Z,16Z)-3-hydroxy-5-[(tetrahydro-2H-pyran-2-yl)oxy]-13,16-docosadienoate and ethyl iodide;

D)c) t-butyl (13Z,16Z)-2-benzyl-3-hydroxy-5-[(tetrahydro-2H-pyran-2-yl)oxy]-13,16-docosadienoate, MS: 525 (M+-(H$_3$C)$_3$CO.) IR: 3498, 1725, 1604, 1585, 1496, 1150 cm$^{-1}$, was obtained
from t-butyl (13Z,16Z)-3-hydroxy-5-[(tetrahydro-2H-pyran-2-yl)oxy]-13,16-docosadienoate and benzyl bromide;

D)d) t-butyl (2S,3S,5R,Z)-2-ethyl-3-hydroxy-5-[(tetrahydro-2H-pyran-2-yl)oxy]docosenoate, MS: 465 (M+-(H$_3$C)$_3$CO.); IR: 3499, 1729, 1155, 1137, 1116 cm$^{-1}$, was obtained
from t-butyl (3S,5R,Z)-3-hydroxy-5-[(tetrahydro-2H-pyran-2-yl)oxy]-13-docosenoate and ethyl iodide;

D)e) t-butyl (2S,3S,5R)-2-ethyl-3-hydroxy-5-(p-phenoxyphenyl)-5-[(tetrahydro-2H-pyran-2-yl)oxy]valerate was obtained
from t-butyl (3S,5R)-3-hydroxy-5-(p-phenoxyphenyl)-5-[(tetrahydro-2H-pyran-2-yl)oxy]valerate and ethyl iodide;

D)f) t-butyl (2S,3S,5R)-2-hexyl-3-hydroxy-5-(p-phenoxyphenyl)-5-[(tetrahydro-2H-pyran-2-yl)oxy]-valerate was obtained
from t-butyl (3S,5R)-3-hydroxy-5-(p-phenoxyphenyl)-5-[(tetrahydro-2H-pyran-2-yl)oxy]valerate and 1-bromohexane;

D)g) t-butyl 2-hexyl-3-hydroxy-(R)-5-[(tetrahydro-2H-pyran-2-yl)oxy]hexadecanoate, D.C. silica gel, hexane-diethyl ether 1:1, Rf=0.65, was obtained
from t-butyl 3-hydroxy-(R)-5-[(tetrahydro-2H-pyran-2-yl)oxy]hexadecanoate and 1-bromohexane.

E) Preparation of the esters of formula VI (variant)

7.76 g of methyl 2-hexyl-3-oxo-5-[(tetrahydro-2H-pyran-2-yl)oxy]hexadecanoate (0.017 mol) were dissolved in 500 ml of THF while gassing with argon, treated with 20 ml of MeOH and cooled to −5° C. 5.3 g of sodium borohydride (0.14 mol) were added portionwise while stirring in such a manner that the temperature did not exceed 0° C. After stirring for 3 hours the excess sodium borohydride was filtered off, the reaction mixture was hydrolyzed (to pH 6) with 2N hydrochloric acid in the cold and the solvent was evaporated off. The residue was extracted with ether and the ethereal phase was dried and evaporated. There were obtained 7.71 g of methyl 2-hexyl-3-hydroxy-5-[(tetrahydro-2H-pyran-2-yl)oxy]hexadecanoate.

F) Preparation of the esters of formula XVII and IX

F)a) 147.6 g of a diastereomer mixture of t-butyl (11Z,14Z)-3-hydroxy-2-[(R)-o-tolylsulfinyl]-11,14-eicosadienoate were dissolved in 5500 ml of THF and then treated within 6 hours with 190 g of amalgamated aluminum foil. In so doing the temperature was held between 15° and 20° C. After completion of the addition the mixture was stirred until the reaction had finished. The insoluble material was filtered off under suction and washed firstly with 1 l of THF, then with 2 l of THF. The filter cake was taken up in 2 l of diethyl ether, stirred and again filtered off under suction. This procedure was repeated once. The combined organic phases were evaporated and the oily residue was purified by chromatography on silica gel, whereby there was obtained an enantiomer mixture which consisted to 80% of t-butyl (R,11Z,14Z)-3-hydroxy-11,14-eicosadienoate, MS: 324 (M+-isobutylene); IR: 3452, 1715, 1154 cm⁻¹.
In an analogous manner, F)b) t-butyl (13Z,16Z)-3-hydroxy-5-[(tetrahydro-2H-pyran-2-yl)oxy]-13,16-docosadienoate, IR: 3481, 1730, 1153, 1075, 1014 cm⁻¹, was obtained
from t-butyl (13Z,16Z)-3-hydroxy-5-[(tetrahydro-2H-pyran-2-yl)oxy]-2-[(S)-p-tolylsulfinyl]-13,14-docosadienoate;

F)c) t-butyl (3S,5R,Z)-3-hydroxy-5-[(tetrahydro-2H-pyran-2-yl)oxy]-13-docosenoate, MS: 437 (M+-(H₃C)₃CO); IR: 3484, 1730, 1655, 1153, 1075, 1024 cm⁻¹, was obtained
from t-butyl (3S,5R,Z)-3-hydroxy-5-[(tetrahydro-2H-pyran-2-yl)oxy]-2-[(S)-p-tolylsulfinyl]-13-docosenoate;

F)d) t-butyl (R,Z)-3-hydroxy-11-eicosenoate, IR: 3445, 1716, 1154 cm⁻¹, was obtained
from t-butyl (R,Z)-3-hydroxy-2-[(R)-p-tolylsulfinyl]-11-eicosenoate;

F)e) t-butyl (3S,5S)-3-hydroxy-5-(p-phenoxyphenyl)-5-[(tetrahydro-2H-pyran-2-yl)oxy]valerate, MS: 357 (M+-tetrahydropyranyl); IR: 3446, 1727, 1590, 1505, 1489, 1152, 1133, 1118, 1074, 1022 cm⁻¹, was obtained
from t-butyl (3S,5S)-3-hydroxy-5-(p-phenoxyphenyl)-5-[(tetrahydro-2H-pyran-2-yl)oxy]-2-[(S)-o-tolylsulfinyl]valerate;

F)f) t-butyl [(S)-α-hydroxy-p-phenoxybenzyl]acetate, m.p. 64°-65° C. (from n-hexane), MS: 314 (M+); IR: 3440, 1713, 1590, 1506, 1491, 1158, was obtained
from t-butyl (βS)-β-hydroxy-p-phenoxy-α-[(R)-p-tolylsulfinyl-hydrocinnamate;

F)g) t-butyl 3-hydroxy-(R)-5-[(tetrahydro-2H-pyran-2-yl)oxy]hexadecanoate was obtained
from t-butyl 3-hydroxy-(R)-5-tetrahydro-2H-pyran-2-yl)oxy]-2-[(S)-p-tolylsulfinyl]hexadecanoate.

G) Preparation of the sulfoxides of formula XI and XVI

G)a) 16.5 g of t-butyl [(S)-p-tolylsulfinyl]acetate were dissolved in a mixture of 600 ml of ether and 60 ml of THF and cooled to −78° C. 43 ml of t-butylmagnesium bromide were then added dropwise in such a manner that the temperature remained below −70° C. After stirring at −78° C. for 1 hour 13.4 g of (R)-3-[(tetrahydro-2H-pyran-2-yl)oxy]-tetradecanal in 100 ml of THF were added dropwise. After 2 hours at −78° C. the reaction mixture was hydrolyzed with 2N hydrochloric acid and the solvent was evaporated off. The reaction mixture remaining behind was extracted with ether and the ethereal phase was dried and evaporated. After chromatography on silica gel there were obtained 14.9 g of t-butyl 3-hydroxy-(R)-5-[(tetrahydro-2H-pyran-2-yl)oxy]-2-[(S)-p-tolylsulfinyl]-hexadecanoate (67% yield). m.p. 97°-98° C.

In an analogous manner.

G)b) t-butyl (3R,11Z,14Z)-3-hydroxy-2-[(R)-p-tolylsulfinyl]-11,14-eicosadienoate, IR: 3400, 1727, 1653, 1596, 1494, 1279, 1258, 1145, 1085, 1045 cm⁻¹, was obtained
from 9,12-octadienal and t-butyl (R)-p-tolylsulfinyl-acetate;

G)c) t-butyl (13Z,16Z)-3-hydroxy-5-[(tetrahydro-2H-pyran-2-yl)oxy]-2-[(S)-p-tolylsulfinyl]-13,16-docosadienoate was obtained
from t-butyl (11Z,14Z)-3-[(tetrahydro-2H-pyran-2-yl)oxy]-11,14-eicosadienal and t-butyl (S)-p-tolylsulfinyl-acetate;

G)d) t-butyl (R,Z)-3-hydroxy-2-[(R)-p-tolylsulfinyl]-11-eicosenoate, MS: 464 (M+isobutylene), IR: 3403, 1727, 1596, 1494, 1145, 1043 cm⁻¹, was obtained
from 9-octenal and t-butyl (R)-p-tolylsulfinyl-acetate;

G)e) t-butyl (3S,5R,Z)-3-hydroxy-5-[(tetrahydro-2H-pyran-2-yl)oxy]-2-[(S)-p-tolylsulfinyl-13-docosenoate was obtained
from t-butyl (R,Z)-3-[(tetrahydro-2H-pyran-2-yl)oxy]-11-eicosenal and (S)-p-tolylsulfinyl-acetate;

G)f) t-butyl (βS)-β-hydroxy-p-phenoxy-α-[(R)-p-tolylsulfinyl]-hydrocinnamate, m.p. 126°-128° C. (from n-hexane), was obtained
from t-butyl p-phenoxy-benzaldehyde and (R)-p-tolylsulfinyl-acetate;

G)g) t-butyl (3S,5S)-3-hydroxy-5-(p-phenoxyphenyl)-5-[(tetrahydro-2H-pyran-2-yl)oxy]-2-[(S)-p-tolylsulfinyl]valerate, m.p. 140°-145° C., was obtained
from t-butyl (βS)-p-phenoxy-β-[(tetrahydro-2H-pyranyl)oxy]-hydrocinnamaldehyde and t-butyl (S)-p-tolylsulfinyl-acetate.

H) Preparation of the alcohols of formula XIII 5 g of a 55% sodium hydride dispersion were washed with hexane and treated with 600 ml of THF. 18.9 g of methyl 2-acetyloctanoate dissolved in 80 ml of THF were added dropwise while cooling. After stirring for 2 hours the mixture was cooled to −10° C. and treated while cooling with 65 ml of butyl lithium (1.6M hexane). After 1 hour at −10° C. a solution of 19.7 g of dodecanal in 80 ml of THF was added dropwise. The mixture was left to warm to room temperature and stirred for a further 2 hours. The reaction mixture was hydrolyzed with 100 ml of 2N hydrochloric acid and evaporated. The residue was extracted with ether and the ethereal phase was dried and evaporated. After chromatography on silica gel there was obtained methyl 2-hexyl-5-hydroxy-3-oxohexadecanoate, m.p. 38°-39° C.

I) Preparation of the aldehydes of formula VIII

I)a) 9.2 g of t-butyl (R)-3-[(tetrahydro-2H-pyran-2-yl)oxy]tetradecanoate were dissolved in 115 ml of toluene while gassing with argon and with the exclusion of moisture and cooled to −75° C. 26.5 ml of a 1.2M solution of diisobutylaluminum hydride in toluene were then added dropwise in such a manner that the temperature did not exceed −70° C. After stirring at −75° C. for 1 hour there were added dropwise 7.4 ml of saturated aqueous ammonium chloride solution and subsequently 15.5 ml of 1N hydrochloric acid at −70° C. The mixture was then left to warm to room temperature. After stirring for 1 hour the organic phase was dried, filtered and evaporated. The material obtained was chromatographed on silica gel. There was obtained (R)-3-[(tetrahydro-2H-pyran-2-yl)oxy]tetradecanal as a colorless oil.

In an analogous manner,

I)b) rac-3-[(tetrahydro-2H-pyran-2-yl)oxy]tetradecanal was obtained
from methyl rac-3-[(tetrahydro-2H-pyran-2-yl)oxy]tetradecanoate;

I)c) (11Z,14Z)-3-[(tetrahydro-2H-pyran-2-yl)oxy]-11,14-eicosadienal, MS: 291 (M+-2-tetrahydropyranyloxy), 290 (M+-tetrahydro-2-pyranol), IR: 2729, 1726, 1132, 1118, 1077 cm$^{-1}$, was obtained
from t-butyl (11Z,14Z)-3-[(tetrahydro-2H-pyran-2-yl)oxy]-11,14-eicosadienoate;

I)d) (R,Z)-3-[(tetrahydro-2H-pyran-2-yl)oxy]-11-eicosanal, MS: 292 (M+-tetrahydro-2-pyranol); IR: 2722, 1726, 1132, 1118, 1077 cm$^{-1}$, was obtained
from t-butyl (R,Z)-3-[(tetrahydro-2H-pyran-2-yl)oxy]-11-eicosanoate;

I)e) (βS)-p-phenoxy-β-[(tetrahydro-2H-pyran-2-yl)oxy]hydrocinnamaldehyde was obtained
from t-butyl [(S)-p-phenoxy-α-[(tetrahydro-2H-pyran-2-yl)oxy]benzyl]acetate;

I)f) (R)-3-[(tetrahydro-2H-pyran-2-yl)oxy]-6Z-tetradecenal was obtained
from ethyl (R)-3-[(tetrahydro-2H-pyran-2-yl)oxy]-6H-tetradecenoate.

J) Preparation of the esters of formula XV

J)a) 66.5 g of t-butyl (R,11Z,14Z)-3-hydroxy-11,14-eicosadienoate, which contained about 20% of the (S)-isomer, and 32 ml of freshly distilled 3,4-dihydro-2H-pyran were dissolved in 650 ml of methylene chloride and cooled to 3° C. Thereafter, 640 mg of p-toluenesulfonic acid monohydrate were added, whereby the temperature rose to 8° C. The mixture was stirred until the reaction was finished. Thereupon, the solution was washed with a mixture of 250 ml of saturated aqueous sodium chloride solution, 250 ml of saturated aqueous sodium hydrogen carbonate solution and 500 ml of water. After drying the mixture was filtered and the solvent was removed. The oily residue was purified by chromatography on silica gel. There was obtained a diastereomer mixture of t-butyl (11Z,14Z)-3-[(tetrahydro-2H-pyran-2-yl)oxy]-11,14-eicosadienoate, MS: 324 (M+-dihydropyran-isobutylene); IR: 1731, 1158, 1024 cm$^{-1}$.

In an analogous manner,

J)b) t-butyl (R,Z)-3-[(tetrahydro-2H-pyran-2-yl)oxy]-11-eicosenoate, MS: 326 (M+-dihydropyran-isobutylene), IR: 1731, 1158, 1134, 1118 cm$^{-1}$, was obtained
from t-butyl (R,Z)-3-hydroxy-11-eicosenoate and dihydropyran;

J)c) t-butyl [(S)-p-phenoxy-α-[(tetrahydro-2H-pyran-2-yl)oxy]benzyl]acetate, MS: 313 (M+-tetrahydropyranyl); IR: 1730, 1590, 1506, 1489, 1391, 1367, 1201, 1149, 1118 cm$^{-1}$, was obtained
from t-butyl [(S)-α-hydroxy-p-phenoxybenzyl]acetate and dihydropyran;

J)d) methyl rac-3-[(tetrahydro-2H-pyran-2-yl)oxy]tetradecanoate, D.C. silica gel, hexane ether 3:1, Rf=0.67, was obtained
from methyl rac-3-hydroxytetradecanoate and dihydropyran;

J)e) methyl 2-hexyl-3-oxo-5-[(tetrahydro-2H-pyran-2-yl)oxy]hexadecanoate, m.p. 37°-38° C., was obtained
from methyl 2-hexyl-5-hydroxy-3-oxo-hexadecanoate and dihydropyran.

K) Preparation of an ester of formula XV (variant)

K)a) A solution of 0.51 g of diisopropylamine in 20 ml of THF was treated at 0° C. with 3.13 ml of a 1.6 molar solution of butyl lithium in hexane. The mixture was then cooled to −78° C. and 2.3 g of heptyltriphenylphosphonium bromide were added thereto and the mixture was left at this temperature for 5 minutes. A solution of ethyl 5-formyl-(R)-3-[(tetrahydro-2H-pyran-2-yl)oxy]pentanecarboxylate in 10 ml of THF was subsequently added dropwise. The mixture was left to stir at room temperature overnight. The reaction mixture was treated with water, extracted with ether, dried and evaporated in vacuo. The residue was chromatographed over silica gel with toluene-ethyl acetate (9:1) and there was obtained 0.5 g of ethyl (R)-3-[(tetrahydro-2H-pyran-2-yl)oxy]-6Z-tetradecenecarboxylate.

K)b) In an analogous manner there was obtained:
Ethyl (R)-3-[(tetrahydro-2H-pyran-2-yl)oxy]-6Z-eicosenecarboxylate.

L) Preparation of an aldehyde of formula XIX

A solution of 2.56 g of methyl (R)-3-[(tetrahydro-2H-pyran-2-yl)oxy]-6-heptenoate in 40 ml of ethyl acetate was treated with ozone at −75° C. After completion of the reaction 0.1 g of Pd-on-carbon was added thereto and the mixture was hydrogenated at room temperature. After the hydrogen uptake was finished the catalyst was filtered off and washed with ethyl acetate and the filtrate and washings were evaporated in vacuo. There was obtained methyl 5-formyl-(R)-3[(tetrahydro-2H-pyran-2-yl)oxy]pentanecarboxylate.

M) Separation of the acids of formula V into their stereoisomers

M)a) 15.4 g of a diastereomer mixture of 2-hexyl-3-hydroxy-(R)-5-[(tetrahydro-2H-pyran-2-yl)oxy]hexadecanoic acid were dissolved in 160 ml of ethanol and 800 mg of toluene-4-sulfonic acid monohydrate were added. The reaction mixture was heated to 55°-60° C. until the reaction was finished. The solvent was removed in vacuo and the residue was dissolved in 160 ml of dichloromethane. The solution was stirred at room temperature for 1 hour. The reaction mixture was evaporated. The material obtained was chromatographed on silica gel. There was obtained tetrahydro-3-hydroxy-(R)-6-undecyl-2H-pyran-2-one, m.p. 95°-96° C.

M)b) 3 g of a diastereomer mixture of tetrahydro-3-hexyl-4-hydroxy-(R)-6-undecyl-2H-pyran-2-one were dissolved in 300 ml of acetone. 3 ml of Jones' reagent were added dropwise while stirring in such a manner that the temperature did not exceed 25° C. After 3 hours the reaction mixture was poured into 700 ml of H$_2$O. The lactone precipitated out and was filtered off. After recrystallization in ether/n-hexane there were obtained 1.7 g of tetrahydro-3-hexyl-4-oxo-(R)-6-undecyl-2H-pyran-2-one, m.p. 112.5°-113.5° C.

M)c) 8 g of an isomer mixture of tetrahydro-3-hexyl-4-oxo-(R)-6-undecyl-2H-pyran-2-one were dissolved in 2 l of ethyl acetate and 3 g of PtO₂ were added. The mixture was then hydrogenated (50 bar) for 12 hours. The catalyst was filtered off and the solution was evaporated. After recrystallization there were obtained 7 g of (3S,4S,6R)-tetrahydro-3-hexyl-4-hydroxy-6-undecyl-2H-pyran-2-one, m.p. 108°-109° C.

M)d) 1.5 g of (3S,4S,6R)-tetrahydro-3-hexyl-4-hydroxy-6-undecyl-2H-pyran-2-one were dissolved in 8 ml of DMF. 0.85 g of t-butyldimethylchlorosilane in 4 ml of DMF were then added dropwise. The mixture was stirred for 48 hours. The reaction mixtures was poured in to 100 ml of ether and washed with 1N hydrochloric acid. The organic phase was dried, filtered and evaporated. The material obtained was chromatographed on silica gel. There was obtained 1.26 g of (3S,4S,6R)-tetrahydro-3-hexyl-4-[(t-butyldimethylsilyl)oxy]-6-undecyl-2H-pyran-2-one, MS: 411 (M+-t-butyl).

M)e) 0.3 g of (3S,4S,6R)-tetrahydro-3-hexyl-4-[(t-butyldimethysilyl)oxy]-6-undecyl-2H-pyran-2-one was dissolved in a mixture of 12 ml of dioxan and 0.64 ml of 1N aqueous potassium hydroxide. The mixture was stirred overnight. The reaction mixture was then evaporated and the residue was dissolved in 10 ml of hexamethylphosphoramide. 0.35 ml of benzyl bromide was added. The mixture was stirred for 2 days. The reaction mixture was poured into water and extracted with ether. The ether phase was dried, filtered and evaporated. The oil was chromatographed on silica gel. There were obtained 330 mg of benzyl (2S,3S,5R)-2-hexyl-3-[(t-butyldimethylsilyl)oxy]-5-hydroxyhexadecanoate, MS: 519 (M+-t-butyl).

M)f) 350 mg of benzyl (2S,3S,5R)-2-hexyl-3-[(t-butyldimethylsilyl)oxy]-5-hydroxyhexadecanoate and 0.5 ml of freshly distilled 3,4-dihydro-2H-pyran were dissolved in 10 ml of methylene chloride and cooled to −15° C. A crystal of p-toluensulfonic acids monohydrate was added thereto. The mixture was stirred until the reaction has finished. Thereupon, the solution was evaporated and the residue was chromatographed on silica gel. There were obtained 330 mg of benzyl (2S,3S,5R)-2-hexyl-3-[(t-butyldimethylsilyl)oxy]-5-[(tetrahydro-2H-pyran-2-yl)oxy]hexandecanoate, MS: 603 (M+-t-butyl).

M)g) 480 mg benzyl (2S,3S,5R)-2-hexyl-3-[(t-butyldimethylsilyl)oxy]-5-[(tetrahydro-2H-pyran-2-yl)oxy]-hexadecanoate and 350 mg of tetrabutylammonium fluoride trihydrate were dissolved in 8 ml of THF and stirred for 12 hours. After evaporation the residue was dissolved in 50 ml of ether and washed with water. The ethereal phase was dried and evaporated. The product was chromatographed on silica gel. There was obtained 240 mg of benzyl (2S,3S,5R)-2-hexyl-3-hydroxy-5-[(tetrahydro-2H-pyran-2-yl)oxy]hexadecanoate, MS: 463 [(M+H)+-dihydro-2H-pyran-2-yl].

M)h) 430 mg benzyl (2S,3S,5R)-2-hexyl-3-hydroxy-5-[(tetrahydro-2H-pyran-2-yl)oxy]hexadecancanoate in 10 ml of THF were treated with Pd/C 10% and hydrogenated for 3 hours. The catalyst was filtered off and, after evaporation of the filtrate, the product was chromatographed on silica gel. There was obtained (2S,3S,5R)-2-hexyl-3-hydroxy-5-[(tetrahydro-2H-pyran-2-yl)oxy]hexadecanoic acid.

The alcohols of formula III in which $R^1$ and $R^2$ are as described above, with the proviso that when $R^1$ is n-hexyl and $R^2$ is undecyl or 2Z,5Z-undecadienyl, at least one of the asymmetric C-atoms present in the oxetanone ring and in the β-position to the latter has the R-configuration, are within the scope of the invention.

Preferred oxetanones of formula I and III are those in which $R^1$ is methyl, propyl, hexyl, decyl, hexadecyl, allyl, benzyl or especially ethyl; $R^2$ is methyl, undecyl, 3-butenyl, 3-undecenyl, 8,11-heptadecadienyl, phenoxyphenyl or especially heptadecyl; $R^3$ is acetyl or especially formyl; $R^4$ is methyl or especially hydrogen and $R^5$ is hydrogen, methyl, 2-butyl, benzyl, methylthioethyl or especially i-butyl, or $R^4$ and $R^5$ together form a pyrrolidinyl residue.

The oxetanones of formula I and III have valuable pharmacological properties. In particular, they inhibit pancreas lipase and can accordingly be used in the control or prevention of obesity, hyperlipaemia, atherosclerosis or arteriosclerosis.

The inhibition of pancreas lipase by the oxetanones of formula I and III can be demonstrated experimentally by registering titrimetrically the oleic acid liberated in the cleavage of triolein by pig pancreas lipase. To an emulsion which contains 1 mM of taurodeoxycholate, 9 mM of taurocholeate, 0.1 mM of cholesterol, 1 mM of egg lecithin, 15 mg/ml of BSA, 2 mM of Tris HCl, 100 mM of sodium chloride, 1 mM of calcium chloride and triolein as the substrate was added the compound of formula I dissolved in ethanol or dimethyl sulfoxide (10% of the emulsion volume) and the reaction was started by the addition of 100 μg (175 U) of pig pancreas lipase. The pH was held at 8 during the reaction by the addition of sodium hydroxide solution. The $IC_{50}$ was calculated from the consumption of sodium hydroxide solution determined during 10 minutes. The $IC_{50}$ was that concentration at which the lipase activity was inhibited to half of the maximum. The following Table contains the $IC_{50}$ values determined for the compounds of formula I and III and data concerning the acute toxicity (toxicity after single oral administration to mice).

TABLE

| Test compound in: | $IC_{50}$ in μg/ml | Toxicity in mg/kg p.o. |
|---|---|---|
| Example 1b) | 19 | |
| Example 2, 13)a) | 0.007 | |
| Example 2, 14) | 0.015 | 5000 |
| Example 2, 21) | 0.02 | |
| Example 2, 23)a) | 0.035 | 2000 |
| Example 2, 25)a) | 0.01 | |
| Example 2, 34) | 0.13 | 4000 |
| Example 4, 1) | 0.011 | |
| Example 5 | 0.20 | |
| Example 6, 2) | 1.0 | |
| Example 7 | 15 | |
| Example 9 F.2. | 85 | |

The oxetanones of formula I and III can be used as medicaments, e.g. in the form of pharmaceutical preparations. The pharmaceutical preparations can be administered orally, e.g. in the form of tablets, coated tablets, dragees, hard and soft gelatine capsules, solutions, emulsions or suspensions.

For the preparation of pharmaceutical preparations the products in accordance with the invention can be processed with pharmaceutically inert, inorganic or organic carrier materials. As such carrier materials there can be used for tablets, coated tablets, dragees and hard gelatine capsules, for example, lactose, maize starch or derivatives thereof, talc, stearic acid or its salts and the like. Suitable carrier materials for gelatine capsules are, for example, vegetable oils, waxes, fats, semisolid and liquid polyols and the like; depending on the nature of the active substances no carrier materials are, however, generally required in the case of soft gelatine capsules. Suitable carrier materials for the manufacture of solutions and syrups are, for example, water, polyols, saccharose, invert sugar, glucose and the like.

Moreover, the pharmaceutical preparations can contain preserving agents, solubilizers, stabilizing agents, wetting agents, emulsifying agents, sweetening agents, coloring agents, flavoring agents, salt for varying the osmotic pressure, buffers, coating agents or antioxidants. They can also contain still other therapeutically valuable substances.

As mentioned earlier, medicaments containing an oxetanone of formula I or III were likewise an object of the present invention as is a process for the manufacture of such medicaments, which process comprises bringing an oxetanone of formula I and III and, if desired, one or more other therapeutically valuble substances into a galenical administration form. As mentioned, the compounds of formula I and III can be used to inhibit pancreas lipase by administration of an effective amount to a host requiring such treatment. Accordingly, the compounds of formula I and III can be used in the treatment, that is, in the control or prevention of illnesses, especially in the control or prevention of obesity, hyperlipaemia, atherosclerosis and arteriosclerosis, by administration of an effective amount to a host requiring such treatment. The dosage can vary within wide limits and is, of course, fitted to the individual requirements in each particular case. In general, in the case of oral administration a daily dosage of about 0.1 mg to 100 mg/kg body weight should be appropriate.

The oxetanones of formula I and II can also be added to industrially-produced foodstuffs, whereby fats, oils, butter, margarine, chocolate and other confectionery goods especially come into consideration. Such industrially-produced foodstuffs, which can contain about 0.1 to 5 wt % of an oxetanone of formula I and III, and their manufacture are likewise objects of the present invention.

The following Examples were intended to illustrate the present invention in more detail, but they are not intended to limit its extent in any manner. All temperatures are given in degrees Celsius.

EXAMPLE 1

44.3 ml of diethyl azodicarboxylate were added dropwise while stirring to a solution of 100 mg of rac-3-hexyl-4-(2-hydroxytridecyl)-2-oxetanone-(2R,3S,4S:2S,3R,4R), 74 mg of triphenylphosphine and 45 mg of N-formyl-D-leucine in 2 ml of THF. After stirring overnight the organic phase was evaporated in vacuo and the residue was purified by chromatography on silica gel with toluene-ethyl acetate (9:1). There were obtained 1.a) N-formyl-D-leucine (R)-1-[[(2R,3R)-3-hexyl-4-oxo-2-oxetanyl]methyl]dodecyl ester and
1.b) N-formyl-D-leucine (S)-1-[[(2S,3S)-3-hexyl-4-oxo-2-oxetanyl]methyl]dodecyl ester.

EXAMPLE 2

Analogously to Example 1,
2.1) by esterifying rac-3-hexyl-4-(2-hydroxytridecyl)-2-oxetanone(2R,3R,4R:2S,3S,4S) with N-formyl-D-leucine there were obtained
2.1)a) N-formyl-D-leucine (S)-1-[[(2R,3R)-3-hexyl-4-oxo-2-oxetanyl]methyl]dodecyl ester and
2.1)b) N-formyl-D-leucine (R)-1-[[(2S,3S)-3-hexyl-4-oxo-2-oxetanyl]methyl]dodecyl ester;
2.2) by esterifying rac-3-hexyl-4-(2-hydroxytridecyl)-2-oxetanone(2S,3R,4R:2R,3S,4S) with formyl-L-leucine there was obtained
N-formyl-L-leucine (R)-1-[[(2R,3R)-3-hexyl-4-oxo-2-oxetanyl]methyl]dodecyl ester, $[\alpha]_D^{25} = -2.2°$ (methanol, c=0.9%);
2.3) by esterifying rac-3-hexyl-4-(2-hydroxytridecyl)-2-oxetanone(2S,3S,4S:2R,3R,4R) or (3R,4R)-3-hexyl-4-[(R)-2-hydroxytridecyl]-2-oxetanone with N-formyl-L-leucine there were obtained.
2.3)a) N-formyl-L-leucine (R)-1-[[(2S,3S)-3-hexyl-4-oxo-2-oxetanyl]methyl]dodecyl ester, $[\alpha]_D^{25} = -19.4°$ (methanol, c=0.35%), and
2.3)b) N-formyl-L-leucine (S)-1-[[(2R,3R)-3-hexyl-4-oxo-2-oxetanyl]methyl]dodecyl ester, $[\alpha]_D^{25} = -2.87°$ (methanol, c=0.8%);
2.4) by esterifying rac-cis-3-hexyl-4-(2-hydroxytridecyl)-2-oxtanone (enantiomer pair A) with N-formyl-L-leucine there were obtained
2.4)a) N-formyl-L-leucine 1-[(cis-3-hexyl-4-oxo-2-oxetanyl)methyl]dodecyl ester, D.C. silica gel; toluene-ethyl acetate 2:1, Rf=0.55, and
2.4)b) N-formyl-L-leucine 1-[(cis-3-hexyl-4-oxo-2-oxetanyl)methyl]dodecyl ester, D.C. silica gel; toluene-ethyl acetate 2:1, Rf=0.47;
2.5) by esterifying rac-cis-3-hexyl-4-(2-hydroxytridecyl)-2-oxetanone (enantiomer pair B) with N-formyl-L-leucine there were obtained
2.5)a) N-formyl-L-leucine 1-[(cis-3-hexyl-4-oxo-2oxetanyl)methyl]dodecyl ester, D.C. silica gel; toluene-ethyl acetate 2:1, Rf=0.53, and
2.5)b) N-formyl-L-leucine 1-[(cis-3-hexyl-4-oxo-2-oxetanyl)methyl]dodecyl ester, D.C. silica gel toluene-ethyl acetate 2:1, Rf=0.50;
2.6) by esterifying (3S,4S)-3-hexyl-4-[(R)-2-hydroxytridecyl]-2-oxetanone with oxetanone with N-formylglycine there was obtained
N-formylglycine (S)-1-(2S,3S)-[(3-hexyl-4-oxo-2-oxetanyl)methyl]dodecyl ester, $[\alpha]_D^{25} = -22°$ (CHCl$_3$, c=0.88);
2.7) by esterifying trans-3hexyl-4-(2-hydroxytridecyl)-2-oxetanone with N-formylglycine there was obtained
N-formylglycine 1-[(trans-3-hexyl-4-oxo-2-oxetanyl)methyl]dodecyl ester, D.C. silica gel, diethyl ester-hexane 9:1; Rf=0.34;
2.8) by esterifying rac-3-hexyl-4-(2-hydroxytridecyl)-2-oxetanone(2R,3S,4S:2S,3R,4R) with N-acetyl-L-leucine there was obtained
N-acetyl-L-leucine 1-[(trans-3-hexyl-4-oxo-2-oxetanyl)methyl]dodecyl ester, D.C. silica gel; CHCl$_3$:hexane:dioxan 1:3:0.25, Rf=0.36;
2.9) by esterifying (3S,4S)-3-hexyl-4-[(R)-2-hydroxytridecyl]-2-oxetanone with N-formyl-β-alanine there was obtained
N-formyl-β-alanine (S)-1-(2S,3S)-[(3-hexyl-4-oxo-2-oxetanyl)methyl]dodecyl ester, D.C. silica gel; toluene-ethyl acetate 2:1, Rf=0.39;
2.10) by esterifying trans-3-hexyl-[(S)-2-hydroxypropyl]-2-oxetanone(3S,4S:3R,4R) with N-formyl-L-leucine there was obtained
N-formyl-L-leucine (S)-1-[(3-hexyl-4-oxo-2-oxetanyl)methyl]ester, D.C. silica gel, toluene-ethyl acetate 2:1, Rf=0.27;

2.11) by esterifying 3-methyl-4-[(R)-2-hydroxytridecyl]-2-oxetanone(3R,4R:3S,4S) with N-formyl-L-leucine there was obtained N-formyl-L-leucine (S)-1-[(3-methyl-4-oxo-2-oxetanyl)methyl]dodecyl ester, D.C. silica gel, toluene-ethyl acetate 2:1, Rf=0.34;

2.12) by esterifying rac-trans-3-hexadecyl-4-(2-hydroxypropyl)-2-oxetanone with N-formyl-L-leucine there was obtained N-formyl-L-leucine 1-[(trans-3-hexadecyl-4-oxo-2-oxetanyl)methyl]ethyl ester, M.S.: 496 (M+; D.C. silica gel, toluene-ethyl acetate 2:1, Rf=0.44;

2.13) by esterifying rac-trans-3-ethyl-4-(2-hydroxytridecyl)-2-oxetanone with N-formyl-L-leucine there were obtained 2.13)a) N-formyl-L-leucine 1-[(trans-3-ethyl-4-oxo-2-oxetanyl)methyl]dodecyl ester, D.C. silica gel, toluene-ethyl acetate 2:1, Rf=0.62, and 2.13)b) N-formyl-L-leucine 1-[(trans-3-ethyl-4-oxo-2-oxetanyl)methyl]dodecyl ester, D.C. silica gel, toluene-ethyl acetate 2:1, Rf=0.55;

2.14) by esterifying rac-trans-3-allyl-4-(2-hydroxytridecyl)-2-oxetanone with N-formyl-leucine there was obtained N-formyl-L-leucine 1-[(trans-3-allyl-4-oxo-2-oxetanyl)methyl]dodecyl ester, I.R.: 1825, 1739, 1688; D.C. silica gel, toluene-ethyl acetate 2:1. Rf=0.58;

2.15) by esterifying rac-trans-3-hexyl-4-(2-hydroxytridecyl)-2-oxetanone with N-benzylcarbamoyl-leucine there was obtained N-benzylcarbamoyl-leucine 1-[(trans-3-hexyl-4-oxo-2-oxetanyl)methyl]dodecyl ester, D.C. silica gel, hexanediethyl ether 1:1, Rf=0.64;

2.16) by esterifying (3S,4S)-3-hexyl-4-[(R,10Z,13Z)-2-hydroxy-10,13-nonadecadienyl)-2-oxetanone with formyl-(S)-leucine there was obtained N-formyl-(S)-leucine(S,9Z,12Z)-1-[[(2S,3S)-3-hexyl-4-oxo-2-oxetanyl]-9,12-octadienyl ester, M.S.: 575 (M+); I.R.: 1824, 1739, 1675 cm$^{-1}$;

2.17) by esterifying rac-trans-3-hexyl-4-[(10Z,13Z)-2-hydroxy-10,13-nonadecadienyl]-2-oxetanone(2R,3R,4R:2S,3S,4S) with N-formyl-(S)-leucine there was obtained N-formyl-(S)-leucine (9Z,12Z)-1-(trans-3-hexyl)-4-oxo-2-oxetanyl)methyl]octadecadienyl ester (2 diastereomers), M.S.: 575 (M+): I.R.: 1824, 1740, 1687 cm$^{-1}$;

2.18) by esterifying cis-3-hexyl-4-[(10Z,13Z)-2-hydroxy-10,13-nonadecadienyl]-2-oxetanone (diastereomer mixture) with N-formyl-(S)-leucine there was obtained 2.18)a) N-formyl-(S)-leucine (9Z,12Z)-1-[(cis-3-hexyl-4-oxo-2-oxetanyl)methyl]-9,12-octadienyl ester (diastereomer mixture I), M.S.: 575 (M+); I.R.: 1823, 1739, 1674 cm$^{-1}$, and 2.18)b) N-formyl-(S)-leucine (9Z,12Z)-1-[(cis-3-hexyl-4-oxo-2-oxetanyl)methyl]-9,12-octadienyl ester (diastereomer mixture II), M.S.: 372 (M+-N-formyl-leucine-CO$_2$); I.R.: 1822, 1739, 1684 cm$^{-1}$;

2.19) by esterifying (3S,4S)-3-benzyl-4-[(R,10Z,13Z)-2-hydroxy-10,13-nonadecadienyl)]-2-oxetanone with N-formyl-(S)-leucine there was obtained N-formyl-(S)-leucine (S,9Z,12Z)-1-[[(2S,3S)-3-benzyl-4-oxo-2-oxetanyl]methyl]-9,12-octadienyl ester, M.S.: 581 (M+); I.R.: 1825, 1739, 1683 cm$^{-1}$;

2.20) by esterifying rac-trans-3-benzyl-4-[(10Z,13Z)-2-hydroxy-10,13-nonadecadienyl]-2-oxetanone(2R,3R,4S:2S,3S,4S) with N-formyl-(S)-leucine there were obtained 2.20)a) N-formyl-(S)-leucine (9Z,12Z)-1-[(trans-3-benzyl-4-oxo-2-oxetanyl)methyl]-9,12-octadecadienyl ester (diastereomer I), M.S.: 581 (M+); I.R.: 1825, 1739, 1676 cm$^{+1}$, and 2.20)b) N-formyl-(S)-leucine (9Z,12Z)-1-[(trans-3-benzyl-4-oxo-2-oxetanyl)methyl]-9,12-octadecadienyl ester (diastereomer II), M.S.: 581 (M+); I.R.: 1824, 1740, 1687 cm$^{-1}$;

2.21) by esterifying trans-3-ethyl-4-[(10Z,13Z)-2-hydroxy-10,13-nonadecadienyl]-2-oxetanone (diastereomer mixture) with N-formyl-(S)-leucine there was obtained N-formyl-(S)-leucine (S,9Z,12Z)-1-[(2S,3S)-3-ethyl-4-oxo-2-oxetanyl]methyl]-9,12-octadecadienyl ester, M.S.: 519 (M+); I.R.: 1825, 1739, 1684 cm$^{-1}$;

2.22) by esterifying cis-3-ethyl-4-[(10Z,13Z)-2-hydroxy-10,13-nonadecadienyl]-2-oxetanone with N-formyl-(S)-leucine (enantiomer mixture B) there was obtained N-formyl-(S)-leucine (9Z,12Z)-1-[[cis-3-ethyl-4-oxo-2-oxetanyl]methyl]-9,12-octadecadienyl ester (diastereomer mixture), M.S.: 316 (M+-N-formyl-leucine-CO$_2$); I.R.: 1825, 1739, 1677 cm$^{-1}$;

2.23) by esterifying (3S,4S)-3-ethyl-4-[(R,Z)-2-hydroxy-10-nonadecenyl]-2-oxetanone with N-formyl-S-leucine there were obtained 2.23)a) N-formyl-(S)-leucine (S,Z)-1-[[(2S,3S)-3-ethyl-4-oxo-2-oxetanyl]methyl]-9-octadecenyl ester (diastereomer I), M.S.: 521 (M+); I.R.: 1825, 1739, 1673 cm$^{-1}$, and 2.23)b) N-formyl-(S)-leucine (Z)-1-[(trans-3-ethyl-4-oxo-2-oxetanyl)methyl]-9-octadecenyl ester;

2.24) by esterifying (3S,4S)-3-hexyl-4-[(S)-β-hydroxy-p-phenoxyphenethyl]-2-oxetanone with N-formyl-(S)-leucine there was obtained N-formyl-(S)-leucine α-[[(2S,3S)-3-hexyl-4-oxo-2-oxetanyl]methyl]-p-phenoxybenzyl ester (diastereomer mixture), M.S.: 509 (M+); I.R.: 1821, 1742, 1686 cm$^{-1}$;

2.25) by esterifying (3S,4S)-3-ethyl-4-[(S)-β-hydroxy-p-phenoxyphenethyl]-2-oxetanone with N-formyl-(S)-leucine there were obtained 2.25)a) N-formyl-(S)-leucine (R)-α-[[(2S,3S)-3-ethyl-4-oxo-2-oxetanyl]methyl]-p-phenoxybenzyl ester, M.S.: 453 (M+); I.R.: 1824, 1742, 1686 cm$^{-1}$, and 2.25)b) N-formyl-(S)-leucine (S)-α-[[(2S,3S)-3-ethyl-4-oxo-2-oxetanyl]methyl]-p-phenoxybenzyl ester, M.S.: 453 (M+); I.R.: 1823, 1743, 1686 cm$^{-1}$;

2.26) by esterifying rac-trans-3-hexyl-4-(2-hydroxy-5-hexenyl)-2-oxetanone with N-formyl-L-leucine there was obtained N-formyl-L-leucine 1-[(trans-3-hexyl-4-oxo-2-oxetanyl)methyl]-4-pentenyl ester (mixture of 2 diastereomers);

2.27) by esterifying (S)-3-hexyl-(S)-4-[(R)-2-hydroxy-5-hexenyl)-2-oxetanone with N-formyl-L-leucine there was obtained N-formyl-L-leucine (S)-1-[[(2S,3S)-3-hexyl-4-oxo-2-oxetanyl]methyl]-4-pentenyl ester;

2.28) by esterifying (S)-3-hexyl-(S)-4-[(R)-2-hydroxy-5-hexenyl)-2-oxetanone with N-formyl-(S)-valine there was obtained N-formyl-(S)-valine 1-[[(2S,3S)-3-hexyl-4-oxo-2-oxetanyl]methyl]-4-pentenyl ester;

2.29) by esterifying (S)-3-hexyl-(S)-4-[(R)-2-hydroxy-5-hexenyl)-2-oxetanone with N-formyl-L-isoleucine there was obtained N-formyl-L-isoleucine (S)-1-[(2S,3S)-3-hexyl-4-oxo-2-oxetanyl]methyl]-4-pentenyl ester;

2.30) by esterifying (S)-3-hexyl-(S)-4-[(R)-2-hydroxy-5-hexenyl)-2-oxetanone with N-formyl-L-phenylalanine there was obtained
N-formyl-phenylalanine (S)-1-[(2S,3S)-3-hexyl-4-oxo-2-oxetanyl)methyl]-4-pentenyl ester;

2.31) by esterifying (S)-3-hexyl-(S)-4-[(R)-2-hydroxy-5-hexenyl)-2-oxetanone with N-formyl-L-alanine there was obtained
N-formyl-L-alanine (S)-1-[(2S,3S)-3-hexyl-4-oxo-2-oxetanyl)-4-pentenyl ester;

2.32) by esterifying (S)-3-hexyl-(S)-4-[(R)-2-hydroxy-5-hexenyl)-2-oxetanone with N-formyl-L-proline there was obtained
N-formyl-L-proline (S)-1-[(2S,3S)-3-hexyl-4-oxo-2-oxetanyl)methyl]-4-pentenyl ester;

2.33) by esterifying (S)-3-hexyl-(S)-4-[(R,Z)-2-hydroxy-5-tridecenyl)-2oxetanone with N-formyl-L-leucine there was obtained
N-formyl-L-leucine (S,Z)-1-[[(2S,3S)-3-hexyl-4-oxo-2-oxetanyl]methyl]-4-dodecenyl ester;

2.34) by esterifying (S)-3-decyl-(S)-4-[(R)-2-hydroxy-5-hexenyl)-2-oxetanone with N-formyl-L-leucine there was obtained
N-formyl-L-leucine (S)-1-[[(2S,3S)-3-decyl-4-oxo-2-oxetanyl]methyl]-4-pentenyl ester;

2.35) by esterifying (S)-3-hexyl-(S)-4-[(R)-2-hydroxy-5-hexenyl]-2-oxetanone with N-formyl-L-methionine there was obtained
N-formyl-L-methionine (S)-1-[(2S,3S)-3-hexyl-4-oxo-2-oxetanyl)methyl]-4-pentenyl ester;

2.36) by esterifying 3-ethyl-4-[(10Z,13Z)-2-hydroxy-10,13-nonadecadienyl)-2-oxetanone with N-formyl-N-methyl-L-leucine there was obtained
N-formyl-N-methyl-L-leucine (9Z,12Z)-1-[(3-ethyl-4-oxo-2-oxetanyl)methyl]-9,12-octadienyl ester.

EXAMPLE 3

A solution of 27 mg of N-formyl-(S)-leucine (S,9Z,12Z)-1-[(2S,3S)-3-hexyl-4-oxo-2-oxetanyl]methyl]-9,12-octadienyl ester in 1 ml of THF was added to 4.4 mg of 10% Pd/C. The mixture was hydrogenated at room temperature until the reaction was finished. The catalyst was filtered off and the solvent was removed in vacuo. After drying in vacuo there was obtained N-formyl-(S)-leucine (S)-1-[[(2S,3S)-3-hexyl-4-oxo-2-oxetanyl]methyloctadecyl ester as white crystals, m.p. 64°-65° C.

EXAMPLE 4

Analogously to Example 3.

4.1) from N-formyl-(S)-leucine (S,9Z,12Z)-1-[(2S,3S)-3-ethyl-4-oxo-2-oxetanyl]methyl]-9,12-octadecadienyl ester there was obtained
N-formyl-(S)-leucine (S)-1-[[(2S,3S)-3-ethyl-4-oxo-2-oxetanyl]methyl]octadecyl ester as white crystals, m.p. 48°-53° C.;

4.2) from N-formyl-L-leucine 1-[(trans-3-allyl-4-oxo-2-oxetanyl]methyl]dodecyl ester there was obtained
N-formyl-L-leucine 1-[(trans-3-propyl-4-oxo-2-oxetanyl]methyl]dodecyl ester.

EXAMPLE 5

A solution of 10 mg of N-formyl-L-leucine 1-[(trans-3-hexyl-4-oxo-2-oxetanyl)methyl]-4-pentenyl ester in 0.5 ml of THF was treated with 2.5 mg of 5% Pd/C and hydrogenated. After the hydrogen uptake was finished the catalyst was filtered off and the filtrate was evaporated in vacuo. The residue was chromatographed over silica gel with toluene/ethyl acetate (8:2) and there was obtained amorphous N-formyl-L-leucine 1-[(trans-3-hexyl-4-oxo-2-oxetanyl]-methyl]pentyl ester as a mixture of 2 diastereomers.

EXAMPLE 6

Analogously to Example 5, 6.1) from N-formyl-L-alanine (S)-1-[[(2S,3S)-3-hexyl-4-oxo-2-oxetanyl]methyl]-4-pentenyl ester there was obtained
N-formyl-L-alanine (S)-1-[[(2S,3S)-3-hexyl-4-oxo-2-oxetanyl]methyl]pentyl ester;

6.2) from N-formyl-L-phenylalanine (S)-1-[(2S,3S)-3-hexyl-4-oxo-2-oxetanyl]methyl]-4-pentenyl ester there was obtained
N-formyl-L-phenylalanine (S)-1-[[(2S,3S)-3-hexyl-4-oxo-2-oxetanyl]methyl]-4-pentyl ester;

6.3) from N-formyl-L-leucine (S)-1-[[(2S,3S)-3-decyl-4-oxo-2-oxetanyl]methyl]-4-pentenyl ester there was obtained
N-formyl-L-leucine (S)-1-[[(2S,3S)-3-decyl-4-oxo-2-oxetanyl]methyl]pentyl ester.

EXAMPLE 7

A solution of 67 mg of N-benzylcarbamoyl-leucine 1-[(trans-3-hexyl-4-oxo-2-oxetanyl)methyldodecyl ester in 15 ml of THF was hydrogenated in the presence of 10% Pd/C at room temperature under a $H_2$ atmosphere (normal pressure) until the reaction was finished. The product obtained after filtration and evaporation was chromatographed on silica gel. There was obtained pure leucine 1-[(trans-3-hexyl-4-oxo-2-oxetanyl)methyl]dodecyl ester m.p. 27°-30° C.

EXAMPLE 8

265 mg of a diastereomer mixture of 3-hexyl-4-[(10Z,13Z)-2-[tetrahydro-2H-pyran-2-yl)-10,13-nonadecadienyl]-2-oxetanone was dissolved in 2.5 ml of ethanol and 13 mg of pyridinium-4-toluenesulfonate were added. The reaction mixture was heated to 55°-60° C. until the reaction was finished. The solvent was removed in vacuo and the residue was taken up in ether, whereby there separated crystals which were removed by filtration. The solvent was evaporated off in vacuo and the residue was chromatographed on silica gel, whereby the products listed below were eluted in the sequence given. The products, which were to some extent still impure, were purified by repeating the chromatography. In this manner there were obtained:

8.1) ((3S,4S)-4-Hexyl-4-[(R,10Z,13Z)-2-hydroxy-10,13-nonadecadienyl]-2-oxetanone (diastereomer I) as a colorless oil, MS: M+ (434); IR: 3420, 1820, 1120 $cm^{-1}$, 8.2) rac-trans-3-hexyl-4-[(10Z,13Z)-2-hydroxy-10,13-nonadecadienyl]-2-oxetanone (diastereomer II) as a colorless oil, MS: M+ (434); IR: 3448, 1820, 1122 $cm^{-1}$ and 8.3) cis-3-hexyl-4-[(10Z,13Z)-2-hydroxy-10,13-nonadecadienyl]-2-oxetanone (diastereomer III) as a colorless oil, MS: M+ (434): IR: 3374, 1822, 1117 $cm^{-1}$.

EXAMPLE 9

Analogously to Example 8,

9.A.1) trans-3-ethyl-4-[(10Z,13Z)-2-hydroxy-10,13-nonadecadienyl]-2-oxetanone, MS: 360 (M+-$H_2O$), 334 ($M^+$-$CO_2$), 316 ($M^+$-$H_2O$-$W_2$), IR: 3446, 1823, 1122 cm$^{-1}$.

9.A.2) cis-3-ethyl-4-[(10Z,13Z)-2-hydroxy-10,13-nonadecadienyl]-2-oxetanone (enantiomer mixture A), MS: 378/$M^+$): IR: 3445, 1822, 1116 cm$^{-1}$ and 9.A.3) cis-3-ethyl-4-[(10Z,13Z)-2-hydroxy-10,13-nonadecadienyl]-2-oxetanone (enantiomer mixture B), MS: (chemical induction with $NH_3$): 396 ($M+NH_4^+$, 374 ($M+H^+$); IR: 3415, 1823, 1115 cm$^{-1}$, were obtained from a cis, trans mixture of 3-ethyl-4-[(R,10Z,13Z)-2-]tetrahydro-2H-pyran-2-yl)oxy]-10,13-nonadecadienyl]-2-oxetanone;

9.B. 3-ethyl-4-[(Z)-2-hydroxy-10-nonadecenyl]-2-oxetanone, MS: 362 ($M^+$-$H_2O$), 318 ($M^+$-$H_2O$-$CO_2$); IR: 3435, 1823, 1119 cm$^{-1}$, was obtained from 3-ethyl-4-[(Z)-2-[(tetrahydro-2H-pyran-2-yl)oxy]-10-nonadecenyl-2-oxetanone;

9.C.1) (3S,4S)-3-benzyl-4-[(R,10Z,13Z)-2-hydroxy-10,13-nonadecadienyl]-2-oxetanone, MS: 440 ($M^+$); IR: 3430, 1822, 1120 cm$^{-1}$, 9.C.2). rac-trans-3-benzyl-4-[(10Z,13Z)-2-hydroxy-10,13-nonadecadienyl]-2-oxetanone, MS: 440 ($M^+$); IR: 3512, 1822, 1123 cm$^{-1}$ and 9.C.3) cis-3-benzyl-4-[(10Z,13Z)-2-hydroxy-10,13-nonadecadienyl]-2-oxetanone (2 diastereomers), MS: 378 ($M^+$-$CO_2$-$H_2O$), 287 ($M^+$-$H_2O$-$CO_2$-benzyl); IR: 3420, 1822, 1134 cm$^{-1}$, were obtained from a diastereomer mixture of 3-benzyl-4-[(R,10Z,13Z)-2-[tetrahydro-2H-pyran-2-yl)oxy]-10,13-nonadecadienyl]-2-oxetanone;

9.D. (3S,4S)-3-hexyl-4-[(S)-β-hydroxy-p-phenoxyphenethyl]-2-oxetanone, m.p. 51°–54° C., MS: 368 ($M^+$); IR: 3486, 1793, 1245, 1141, was obtained from (3S,4S)-3-hexyl-4-[(S)-p-phenoxy-β-[(tetrahydro-2H-pyran-2-yl)oxy]phenethyl]-2-oxetanone.

9.E. (3S,4S)-3-ethyl-4-[(S)-β-hydroxy-p-phenoxyphenethyl]-2-oxetanone, m.p. 67°–70° C., MS: 312 ($M^+$); IR; 3416, 1835, 1250, 1108, was obtained from (3S,4S)-3-ethyl-4-[(S)-p-phenoxy-β-[(tetrahydro-2H-pyran-2-yl)oxy]phenethyl]-2-oxetanone.

9.F.1. rac-trans-3-hexyl-4-(2-hydroxytridecyl)-2-oxetanone(2R,3S,4S:2S,3R,4R), m.p. 44.5°–46°, 9.F.2. rac-trans-3-hexyl-4-(2-hydroxytridecyl)-2-oxetanone(2S,3S,4S:2R,3R,4R), m.p. 45.5°–47° C., 9.F.3. rac-cis-3-hexyl-4-(2-hydroxytridecyl)-2-oxetanone (enantiomer pair A), D.C. silica gel, hexane-ethyl acetate 9:1, Rf=0.49, and 9.F.4. rac-cis-3-hexyl-4-(2-hydroxytridecyl)-2-oxetanone (enantiomer pair B), D.C. silica gel, hexane-ethyl acetate 9:1, Rf=0.46, were obtained from 3-hexyl-4-[2-[(tetrahydro-2H-pyran-2-yl)oxy]-tridecyl]-2-oxetanone;

9.G.1. (3S,4S)-3-hexyl-4-[(R)-2-hydroxytridecyl]-2-oxetanone, m.p. 46°–46.5° C., and 9.G.2. (3R,4R)-3-hexyl-4-[(R)-2-hydroxytridecyl]-2-oxetanone, m.p. 46°–47°; $[\alpha]_D^{20}$=+12° C. ($CHCl_3$, c=1.5), were obtained from 3-hexyl-4-[(R)-2-[(tetrahydro-2H-pyran-2-yl)oxy]-tridecyl]-2-oxetanone;

9.H. rac-trans-3-ethyl-4-(2-hydroxytridecyl)-2-oxetanone, m.p. 35.5°–36° C., was obtained from 3-ethyl-4-[2-[(tetrahydro-2H-pyran-2-yl)oxy]-tridecyl]-2-oxetanone;

9.I. trans-3-methyl-4-[(R)-2-hydroxytridecyl]-2-oxetanone, D.C. silica gel, hexane-ether 1:3, Rf=0.49, was obtained from 3-methyl-4-[(R)-2-[(tetrahydro-2H-pyran-2-yl)oxy]tridecyl]-2-oxetanone;

9.J. rac-trans-3-allyl-4-[2-hydroxytridecyl]-2-oxetanone, D.C. silica gel, hexane ether 1:1, Rf=0.39, was obtained from 3-allyl-4-[2-(tetrahydro-2H-pyran-2-yl)oxy]-tridecyl]-2-oxetanone;

9.K. trans-3-hexyl-4-[(R)-2-hydroxypropyl]-2-oxetanone, D.C. silica gel, hexane-ether 1;3, Rf=0.36, was obtained from 3-hexyl-4-[(R)-2-[(tetrahydro-2H-pyran-2-yl)oxy]-propyl]-2-oxetanone;

9.L. rac-trans-3-hexadecyl-4-(2-hydroxypropyl)-2-oxetanone, m.p. 37°–18° C., was obtained from 3-hexadecyl-4-[2-[(tetrahydro-2H-pyran-2-yl)oxy]propyl]-2-oxetanone;

9.M. rac-trans-3-hexyl-4-[-2-hydroxy-5-hexenyl]-2-oxetanone(2R,3S,4S:2S,3R,4R) was obtained from trans-3-hexyl-4-]-2-[(tetrahydro-2H-pyran-2-yl)oxy]-5-hexenyl]-2-oxetanone;

9.N. trans-3-decyl-4-[(R)-2-hydroxy-5-hexenyl-2-oxetanone was obtained from trans-3-decyl-4-[(R)-2-[(tetrahydro-2H-pyran-2-yl)oxy]hexenyl]-2-oxetanone;

9.O. trans-3-hexyl-4-((R)-2-hydroxy-5-tridecenyl)-2-oxetanone was obtained from trans-3-hexyl-4-[(R)-2-[(tetrahydro-2H-pyran-2-yl)oxy]tridecenyl-2-oxetanone;

9.P. (S)-3-hexyl-(S)-4-[(R)-2-hydroxy-5-hexenyl]-2-oxetanone was obtained from 3-hexyl-4-[[(R)-2-[(tetrahydro-2H-pyran-2-yl)oxy]hexenyl]-2-oxetanone;

9.Q. trans-3-hexyl-4-(2-hydroxytridecyl)-2-oxetanone (diastereomer mixture) was obtained from 3-hexyl-4-[2-[tetrahydro-2H-pyran-2-yl)oxy]-tridecyl]-2-oxetanone.

EXAMPLE 10

10.A. Manufacture of the product 565 mg of N-[(benzyloxy)carbonyl]-L-leucine (S)-1-[[(2S,3S)-3-ethyl-4-oxo-2-oxetanyl]methyl]octadecyl ester were dissolved in 12 ml of THF. The mixture was hydrogenated at room temperature in the presence of 40 mg of 10% Pd/C. After the reaction was finished the catalyst was filtered off and the filtrate was evaporated. The residue was taken up in 9 ml of THF and 71 μl of formic acid/acetic acid anhydride were added dropwise. The mixture was diluted with 5 ml of diethyl ether and washed twice with 2% sodium hydrogen carbonate solution and then with water. After drying over sodium sulfate it was filtered and evaporated. By chromatography on silica gel and recrystallization from n-pentane there was obtained N-formyl-(S)-leucine (S)-1-[[(2S,3S)-3-ethyl-4-oxo-2-oxetanyl]methyl]octadecyl ester of m.p. 60°–61° C.

10.B. Preparation of the starting material

10.B.a) As described in paragraph 10.B.e) hereinafter, a diastereomer mixture which consisted of 85–90% of (R)-2-hydroxy-1,2,2-triphenylethyl (S,Z)-3-hydroxy-11-eicosenoate, m.p. 112°–114° C., was obtained from oleyl aldehyde and (R)-α-(hydroxydiphenylmethyl)benzyl acetate.

10.B.b) As described in paragraph 10.B.f) hereinafter, methyl (S,Z)-3-hydroxy-11-eicosenoate was obtained as a colorless oil from (R)-2-hydroxy-1,2,2-triphenylethyl(S,Z)-3-hydroxy-11-eicosenoate.

10.B.c) As described in paragraph J)a) above for the preparation of the esters of formula XV, methyl (S,Z)-3-[(tetrahydro-2H-pyran-2-yl)oxy]-11-eicosenoate, which contained 10–15% of the (R)-isomer, was obtained from methyl (S,Z)-3-hydroxy-11-eicosenoate.

10.B.d) As described in paragraph I)a) above for the preparation of the aldehydes of formula VIII, (S,Z)-3-[(tetrahydro-2H-pyran-2-yl)oxy]-11-eicosenal, which contained 10–15% of the corresponding (R)-isomer, was obtained from methyl (S,Z)-3-[(tetrahydro-2H-pyran-2-yl)oxy]-11-eicosenoate.

10.B.e) 7.7 g of (R)-α-(hydroxydiphenylmethyl)benzyl acetate were suspended in 75 ml of THF under argon and cooled to about −75° C. This suspension was treated dropwise with a two-fold amount of a lithium diisopropylamide solution. The mixture was left to warm to 0° C. and stirred at this temperature for 10 minutes. The solution was then cooled to −113° to −117° C. and treated during the cooling with 230 ml of diethyl ether. A solution of (S,Z)-3-[(tetrahydro-2H-pyran-2-yl)oxy]-11-eicosenal in 20 ml of diethyl ether was added dropwise to the solution and the mixture was stirred for a further 30 minutes. The mixture was treated dropwise with 20 ml of saturated ammonium chloride solution. The mixture was left to warm to room temperature. The aqueous phase was separated and the organic phase was washed three times with 80 ml of water and once with saturated sodium chloride solution. After two-fold washing with 100 ml of saturated ammonium chloride solution the organic phase was dried over sodium sulfate, filtered and evaporated. By repeated recrystallization from methanol there was obtained a diastereomer mixture which consisted mainly of (R)-2-hydroxy-1,2,2-triphenylethyl(3S,5S,13Z)-3-hydroxy-5-[(tetrahydro-2H-pyran-2-yl)oxy]-13-docosenoate, m.p. 91°–93° C.

10.B.f) 12.75 g of (R)-2-hydroxy-1,2,2-triphenylethyl(3S,5S,13Z)-3-hydroxy-5-[(tetrahydro-2H-pyran-2-yl)oxy]-13-docosenoate were suspended in 130 ml of methanol and treated with 17.5 ml of 1N methanolic sodium methylate solution. After the reaction was finished the mixture was poured into 650 ml of saturated ammonium chloride solution and extracted several times with diethyl ether. After drying over sodium sulfate the organic phase was filtered and evaporated, the residue was taken up in 70 ml of n-hexane and stirred for 1 hour while cooling in an ice-bath. The white crystals were filtered off under suction and washed with n-hexane. The filtrate was evaporated and the residue was chromatographed on silica gel. There was obtained a diastereomer mixture which consisted chiefly of methyl (3S,5S,13Z)-3-hydroxy-5-[(tetrahydro-2H-pyran-2-yl)oxy]-13-docosenoate, IR: 3473, 1739, 1076, 1024 cm$^{-1}$.

10.B.g) As described in paragraph D)a) above for the preparation of the esters of formula VI, a diastereomer mixture, which contained chiefly methyl (2S,3S,5S,13Z)-2-ethyl-3-hydroxy-5-[(tetrahydro-2H-pyran-2-yl)oxy]-13-docosenoate, was obtained as a colorless oil from methyl (3S,5S,13Z)-3-hydroxy-5-[(tetrahydro-2H-pyran-2-yl)oxy]-13-docosenoate and ethyl iodide.

10.B.h) In analogy to Example 3 above, a diastereomer mixture, which contained chiefly methyl (2S,3S,5S)-2-ethyl-3-hydroxy-5-[(tetrahydro-2H-pyran-2-yl)oxy]docosanoate, IR: 1738, 1199, 1167, 1132, 1115, 1176, 1023 cm$^{-1}$, was obtained from a diastereomer mixture which consisted chiefly of methyl (2S,3S,5S,13Z)-2-ethyl-3-hydroxy-5-[(tetrahydro-2H-pyran-2-yl)oxy]-13-docosenoate.

10.B.i) 0.12 g of a diastereomer mixture, which consisted chiefly of methyl (2S,3S,5S)-2-ethyl-3-hydroxy-5-[(tetrahydro-2H-pyran-2-yl)oxy]docosanoate, was stirred at room temperature in 2.5 ml of 2N methanolic potassium hydroxide solution until the reaction was finished. The turbid solution was poured into 10 ml of water and adjusted to pH 2 with 2N hydrochloric acid. After extraction with diethyl ether the extract was dried over sodium sulfate, filtered and evaporated. Chromatography on silica gel gave a diastereomer mixture which consisted chiefly of (2S,3S,5S)-2-ethyl-3-hydroxy-5-[(tetrahydro-2H-pyran-2-yl)oxy]docosanoic acid as a colorless oil, IR: 1709 cm$^{-1}$.

10.B.j) As described in paragraph A.a) above for the preparation of the ethers of formula IV, (3S,4S)-3-ethyl-4-[(S)-2-[(tetrahydro-2H-pyran-2-yl)oxy]nonadecyl]-2-oxetanone was obtained as the main component of a diastereomer mixture as a colorless oil, IR: 1826 cm$^{-1}$, from a diastereomer mixture which consisted chiefly of (2S,3S,5S)-2-ethyl-3-hydroxy-5-[(tetrahydro-2H-pyran-2-yl)oxy]docosanoic acid.

10.B.k) In analogy to Example 8, (3S,4S)-3-ethyl-4-[(S)-2-hydroxynonadecyl]-2-oxetanone, m.p. 82°–84° C. (MeOH), was obtained from (3S,4S)-3-ethyl-4-[(S)-2-[(tetrahydro-2H-pyran-2-yl)oxy]nonadecyl]-2-oxetanone.

10.B.l) 796 mg of N-[(benzyloxy)carbonyl]-L-leucine were dissolved in 10 ml of methylene chloride, the solution was cooled to 2°–3° C. and 309 mg of dicyclohexylcarbodiimide were added. After 15 minutes the white crystals were filtered off under suction and washed with methylene chloride. The filtrate was evaporated at room temperature in vacuo and the residue was dissolved in 7 ml of N,N-dimethylformamide (DMF). This solution was added to 574 mg of (3S,4S)-3-ethyl-4-[(S)-2-hydroxynonadecyl]-2-oxetanone and 22 mg of 4-dimethyl-amino-pyridine in 6 ml of DMF. The mixture was stirred for 30 minutes. The mixture was poured on to 100 ml of ice-water and extracted three times with 20 ml of diethyl ether. The combined organic phases were dried over sodium sulfate, filtered and evaporated. After chromatography on silica gel there was obtained N-[(benzyloxy)carbonyl]-L-leucine (S)-1-[[(2S,3S)-3-ethyl-4-oxo-2-oxetanyl]methyl]octadecyl ester as white crystals of m.p. 44°–47° C.

EXAMPLE A

Manufacture of soft gelatine capsules of the following composition:

| | Amount per capsule | |
|---|---|---|
| An oxetanone of formula I or III | 50 | mg |
| NEOBEE M-5 | 450 | μl |

The solution of the active substance in NEOBEE M-5 is filled into soft gelatine capsules of suitable size.

NEOBEE M-5 is fractionated coconut oil.

We claim:

1. A method for treating obesity, hyperlipaemia, atherosclerosis or arteriosclerosis which comprises administering to a host requiring such treatment an effective amount of a racemic compound of the formula

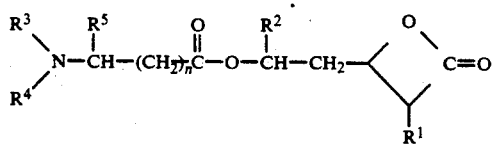

wherein $R^1$ and $R^2$ are independently $C_{1-17}$-alkyl which is saturated or optionally interrupted by up to 8 double or triple bonds and/or optionally interrupted by and O or S atom which is present in a position other than the α-position to an unsaturated C-atom; or phenyl, benzyl or —$C_6H_4$—X—$C_6H_5$ ring-substituted by up to 3 $C_{1-6}$-alkyl-(O or S) $_{1 \, or \, 0}$ groups, X is oxygen, sulfur or ($CH_2$)$_{0-3}$, $R^3$ is hydrogen, $C_{1-3}$-alkyl or $C_{1-3}$-alkanoyl, $R^4$ is hydrogen or $C_{1-3}$-alkyl, and $R^5$ is hydrogen, a group Ar or Ar-$C_{1-3}$-alkyl or $C_{1-7}$-alkyl optionally interrupted by Y and optionally substituted by Z, or $R^4$ forms with $R^5$ a 4- to 6-membered saturated ring, Y is oxygen, sulfur or a group N($R^6$), C(O)N($R^6$) or N($R^6$)C(O), Z is a group —(O or S)—$R^7$, —N($R^7$,$R^8$), —C(O)N($R^7$,$R^8$) or —N($R^7$)C(O)$R^8$, n is the number 1 or 0, with the proviso that $R^5$ is hydrogen when n is the number 1, Ar is phenyl which is unsubstituted or substituted by up to 3 groups $R^9$ or O$R^9$, and $R^6$, $R^7$, $R^8$ and $R^9$ individually are hydrogen or $C_{1-3}$-alkyl, with the proviso that $R^4$ is other than hydrogen when $R^3$ is formyl and $R^5$ is isobutyl or $R^3$ is acetyl and $R^5$ is carbamoylmethyl, and simultaneously $R^2$ is undecyl or 2,5-undecadienyl and $R^1$ is n-hexyl, an enantiomer or a diastereomer thereof, or a pharmaceutically acceptable acid addition salt thereof.

2. The method according to claim 1, wherein $R^1$ is methyl, propyl, hexyl, decyl, hexadecyl, allyl, benzyl or ethyl; $R^2$ is methyl, undecyl, 3-butenyl, 3-undecenyl, 8,11-heptadecadienyl, phenoxyphenyl or heptadecyl; $R^3$ is acetyl or formyl; $R^4$ is methyl or hydrogen and $R^5$ is hydrogen, methyl, 2-butyl, benzyl, methylthioethyl or i-butyl, or $R^4$ and $R^5$ together form a pyrrolidinyl moiety.

3. The method in accordance with claim 1, wherein the compound of formula I is N-formyl-(S)-leucine (S)-1-[[(2S,3S)-3-ethyl-4-oxo-2-oxetanyl]methyl]octadecyl ester, or a pharmaceutically acceptable acid addition salt thereof.

4. The method in accordance with claim 1, wherein the compound of formula I is selected from the group consisting of:

N-formyl-L-leucine 1-[(trans-3-ethyl-4-oxo-2-oxetanyl)methyl]dodecyl ester

N-formyl-L-leucine 1-[(trans-3-allyl-4-oxo-2-oxetanyl)methyl]dodecyl ester

N-formyl-(S)-leucine (S,9Z,12Z)-1-[(2S,3S)-3-ethyl-4-oxo-2-oxetanyl]methyl]-9,12-octadecadienyl ester N-formyl-(S)-leucine (S,Z)-1-[[(2S,3S)-3-ethyl-4-oxo-2-oxetanyl]methyl]-9-octadecenyl ester and N-formyl-(S)-leucine (R)-α-[[(2S,3S)-3-ethyl-4-oxo-2-oxetanyl]methyl]-p-phenoxybenzyl ester; or a pharmaceutically acceptable acid addition salt thereof.

5. The method according to claim 2, wherein $R^1$ is ethyl.

6. The method according to claim 2, wherein $R^2$ is heptadecyl.

7. The method according to claim 2, wherein $R^3$ is formyl.

8. The method according to claim 2, wherein $R^4$ is methyl.

9. The method according to claim 2, wherein $R^5$ is i-butyl.

* * * * *